United States Patent [19]
Gilmore et al.

[11] Patent Number: 5,955,671
[45] Date of Patent: Sep. 21, 1999

[54] METHOD AND APPARATUS FOR MEASUREMENT OF ORIENTATION IN AN ANISOTROPIC MEDIUM

[75] Inventors: Robert Snee Gilmore, Burnt Hills, N.Y.; Ronald Alan Kline, Norman, Okla.; John Broddus Deaton, Jr., Niskayuna, N.Y.

[73] Assignee: General Electric Company, Schenectady, N.Y.

[21] Appl. No.: 08/826,252

[22] Filed: Mar. 28, 1997

[51] Int. Cl.⁶ .................................................. G01N 29/18
[52] U.S. Cl. .................................. 73/597; 73/602; 73/620
[58] Field of Search ............................ 73/602, 597, 598, 73/599, 600, 620, 630, 627, 628

[56] References Cited

U.S. PATENT DOCUMENTS

| | | | |
|---|---|---|---|
| 4,106,327 | 8/1978 | Adler et al. | 73/597 |
| 4,893,510 | 1/1990 | Ichikawa et al. | 73/620 |
| 5,209,123 | 5/1993 | Prosser et al. | 73/788 |
| 5,337,610 | 8/1994 | Prosser et al. | 73/599 |
| 5,408,882 | 4/1995 | Mckinley et al. | 73/597 |

OTHER PUBLICATIONS

"Ultrasonic Orientation Determination of Single Crystals" by R.E. Green, Jr., & G. Henneke, II, Dept. of Mechanics, The Johns Hopkins University, Baltimore, Maryland, vol. 41, No.1 (1967) pp. 84–90.

"Crystal Acoustics" by M.J.P. Musgrave–Reader in Applied Mathematics, Imperial College, London, Chapter 6(pp. 66–82) and Chapter 7 (pp. 83–93) (1970).

"Theory of Elastic Waves in Crystals" by Fedor I. Fedorov, Belorrusian State Univeresity, Minsk, Chapter 4(pp.119–167) and Chapter 7 (pp. 245–282) (1968).

"Ultrasonic Investigation of Mechanical Properties", by Robert E. Green, Jr., Treatise on Materials Science and Technology, vol. 3 Chapter I (pp. 1–2) and Chapter II (pp.3–72) (1973).

"Stress Waves in Solids" by H. Kolsky, Chapter IV (pp.95–98) and Chapter VI (pp. 130–162) (1953).

"Nondestructive Characterization of Composite Media" by Ronald A. Kline, Chapters 1–10 (pp. 1–175) (1992).

"Ultrasonic Double Refraction in Worked Metals"by Paul F. Sullivan and Emmanuel P. Papadakis, The Journal of the Acoustical Society of America, vol. 33, No.11, Nov. 1961 (1622–1624).

"Calculation of Elastic Anisotropy in Rolled Sheet" by G.A. Alers and Y.C. Liu, Transactions of the Metallurgical Society of AIME, vol. 236, Apr. 1966, (pp.482–489).

"Texture of Polycrystalline Metals Characterized by Ultrasonic Velocity Measurements" by M. Hirao, K. Aoki, and H. Fukuoka, H. Acoust. Soc. Am., vol. 81, No. 5, May 1987 (pp. 1434–1440).

"Relations Between Elastic Constants $C_{ij}$ and Texture Parameters for Hexagonal Materials"by Yan Li and R. Bruce Thompson, J. Appl. Phys., vol. 67, No. 5, Mar. 1990, (pp. 2663–2665).

(List continued on next page.)

*Primary Examiner*—Hezron E. Williams
*Assistant Examiner*—Rose M. Miller
*Attorney, Agent, or Firm*—Tyler Maddry; Noreen C. Johnson

[57] ABSTRACT

A method and apparatus are provided for simultaneously measuring the anisotropic orientation and the thickness of an article. The apparatus comprises a transducer assembly which propagates longitudinal and transverse waves through the article and which receives reflections of the waves. A processor is provided to measure respective transit times of the longitudinal and shear waves propagated through the article and to calculate respective predicted transit times of the longitudinal and shear waves based on an estimated thickness, an estimated anisotropic orientation, and an elasticity of the article. The processor adjusts the estimated thickness and the estimated anisotropic orientation to reduce the difference between the measured transit times and the respective predicted transit times of the longitudinal and shear waves.

42 Claims, 22 Drawing Sheets

OTHER PUBLICATIONS

"Simultaneous Measurement of the Acoustical Properties of a Thin–Layered Medium: The Inverse Problem" by V.K. Kinra, P.T. Jaminet, C. Zhu, and V.R. Iyer, J. Acoust. Soc. Am., vol. 95 No. 6. Jun. 1994 (pp. 3059–3074).

"A Method for the Solution of Certain Non–Linear Problems in Least Squares" by Kenneth Levenberg, 2 Quarterly of Appl. Math. (pp. 164–168) 1944.

"An Algorithm for Least–Squares Estimation of Nonlinear Parameters" by Donald W. Marquardt, J. Soc. Indust. Appl. Math., vol. 11, No. 2, Jun. 1963, (pp. 431–441).

"Industrial Ultrasonic Imaging and Microscopy" by R.S. Gilmore, 29 J. Phys. D: Appl. Phys. (1996) (pp. 1389–1417).

IMSL, Inc., FORTRAN Subroutines for Mathematical Applications User's Manual, 8.1.3(pp. 1023–1029) (1991).

METHOD AND APPARATUS FOR MEASUREMENT OF ORIENTATION IN AN ANISOTROPIC MEDIUM

The U.S. Government may have rights in this invention pursuant to Contract No. DE-FC21-95MC31176 awarded by the U.S. Department of Energy.

BACKGROUND

1. Field of the Invention

The present invention relates generally to the measurement of thickness and orientation of an article, and more particularly to a method and apparatus for determining the anisotropic orientation and thickness of an article formed of an anisotropic material.

2. Description of the Related Art

It is known that anisotropic materials such as those formed of a single metallic crystal can offer significant advantages in certain engineering applications. For example, a structural component made of a single crystal may be significantly stronger than a component formed of a polycrystalline material, due to the relatively weak junction between crystals or "grains" in the polycrystalline material. The absence of such junctions in an anisotropic, single crystal component is especially important in high temperature applications, where the strength of the junction is further diminished.

In using anisotropic materials for manufacturing, however, it is often important to ensure that the material is properly aligned in its finished state. Since the material properties can be highly directionally dependent, small deviations in crystal orientation can result in significant changes in the mechanical response of the component and its ability to perform as designed, for example in high temperature or high stress applications. With the advent of anisotropic, single crystal components in critical, load bearing areas, the ability to characterize orientation nondestructively is important to ensuring the quality of such components.

Another area in which it is often important to ensure the proper alignment of an anisotropic component is in machining. Many structural materials, while statistically isotropic in their original form, are produced in rolling or extrusion operations, which results in an anisotropy due to a preferential alignment in the grain structure. For some of these materials, e.g. titanium, knowledge of the material anisotropy may be critical to the efficient machining of the component.

Conventional methods for determining the crystal orientation of an isotropic material typically utilize x-ray diffraction, in which the interference pattern of diffracted x-ray radiation is used to reconstruct the crystal orientation. While x-ray diffraction methods are generally accurate and nondestructive, each measurement is very time consuming. In addition, only the material properties at the surface of the article are measured. X-ray diffraction methods are therefore impractical unless it is feasible to cut a small portion from the sample for testing, in which case the method is no longer nondestructive.

Another known method for determining the crystal orientation in an article formed of a single crystal material is described in Green et al, *Ultrasonic Orientation Determination of Single Crystals,* 41 Journal of the Accoustical Society of America 84 (1967). This method involves compiling a table of values for the velocities of shear and longitudinal waves propagated a priori through a sample of the single crystal material. The velocity values are plotted on a standard stereographic triangle as a function of the direction of propagation, as shown for example in FIGS. 1*a*–1*c*, where FIG. 1*a* is a longitudinal wave, FIG. 1*b* is a slow shear wave and FIG. 1*c* is a fast shear wave. Since every distinct crystal orientation is associated with a unique combination of longitudinal and shear wave velocities, a measurement of these values on the article to be tested can be used to find the crystal orientation of the article by overlaying any two of the three stereographic triangles. The velocities of the waves through the article may be obtained by measuring the transit times of longitudinal and shear waves reflected off the back surface of the article.

The Green et al method, however, requires that the thickness of the article be known independently to calculate velocity, as only transit time is measured. The method is unavailable, therefore, in applications where the thickness cannot be measured. Although methods for nondestructive measurement of the thickness of an article, e.g. ultrasonic methods, are well known, such devices typically utilize a known velocity of sound propagation in conjunction with a measured transit time to extract the distance traveled by the wave, i.e., the thickness. These devices, however, are generally applicable only to isotropic media, and can be very inaccurate when the velocity of sound changes with the propagation direction, as in an anisotropic material. Thus, when both the crystal orientation and the thickness are unknown, a new approach is needed to avoid errors arising from the intrinsic variation in velocity due to anisotropy.

Another significant shortcoming of the Green et al method is that it is a graphical method which involves overlaying two stereographic triangle plots and finding an intersection point between two velocity curves to determine the crystal orientation. As such, there is an inherent uncertainty associated with manually locating the contour intersection points on the two stereographic triangles. This places stringent limits on the precision in the velocity measurement needed to orient a typical crystal, particularly if the degree of anisotropy is relatively small. Green et al estimate that the acoustic velocities must be measured to within an accuracy of 0.1% for the method to be useful. This degree of measurement accuracy may be difficult to achieve in many applications. This shortcoming, along with the cumbersome nature of the stereographic plot manipulations, has precluded its use in practice.

SUMMARY

There is a particular need in the art, therefore, for a method and apparatus for measuring an orientation of an anisotropic article with improved accuracy. According to an exemplary embodiment of the invention, the apparatus comprises means for propagating a first wave and a second wave through the article; means for measuring a respective transit time of the first wave and the second wave propagating through the article; means for calculating a respective predicted transit time of the first wave and the second wave based on an estimated anisotropic orientation and an elasticity of the article; and means for adjusting the estimated anisotropic orientation to reduce a difference between the respective measured transit time and the respective predicted transit time of the first and second waves.

According to another exemplary embodiment of the invention, a method and apparatus are provided in which the orientation and the thickness of the article may be determined simultaneously. An exemplary apparatus according to this embodiment comprises a transducer assembly which generates first, second, and third waves in the article and which receives reflections of the first, second and third waves; a transceiver, connected to the transducer, which generates a signal to activate the transducer assembly and which receives a signal representative of the reflections of the first, second, and third waves from the transducer assembly; and a computer, connected to the transceiver, which commands the transceiver to generate the signal to activate the transducer and which receives from the transceiver a signal representative of the reflections of the first, second, and third waves, the computer being adapted to determine respective transit times for the first, second and third waves; receive estimated values for the thickness and the anisotropic orientation of the article; receive elastic properties of the article; calculate respective predicted transit times of the first, second, and third waves based on the estimated values for the thickness and the anisotropic orientation and based on the elastic properties; and adjust the estimated values for the thickness and the anisotropic orientation to reduce a difference between the respective measured transit time and the respective predicted transit time of the first, second and third waves.

According to another aspect of the invention, the above devices and methods may be modified to compensate for the effects of "beam skew" in an anisotropic material, so that the thickness of an article which has a curved surface may be accurately measured.

BRIEF DESCRIPTION OF THE DRAWINGS

Additional features and advantages of the invention will be apparent upon reading the following detailed description in conjunction with the accompanying drawings in which.

DETAILED DESCRIPTION OF THE PREFERRED EMBODIMENTS

Figure 1A:
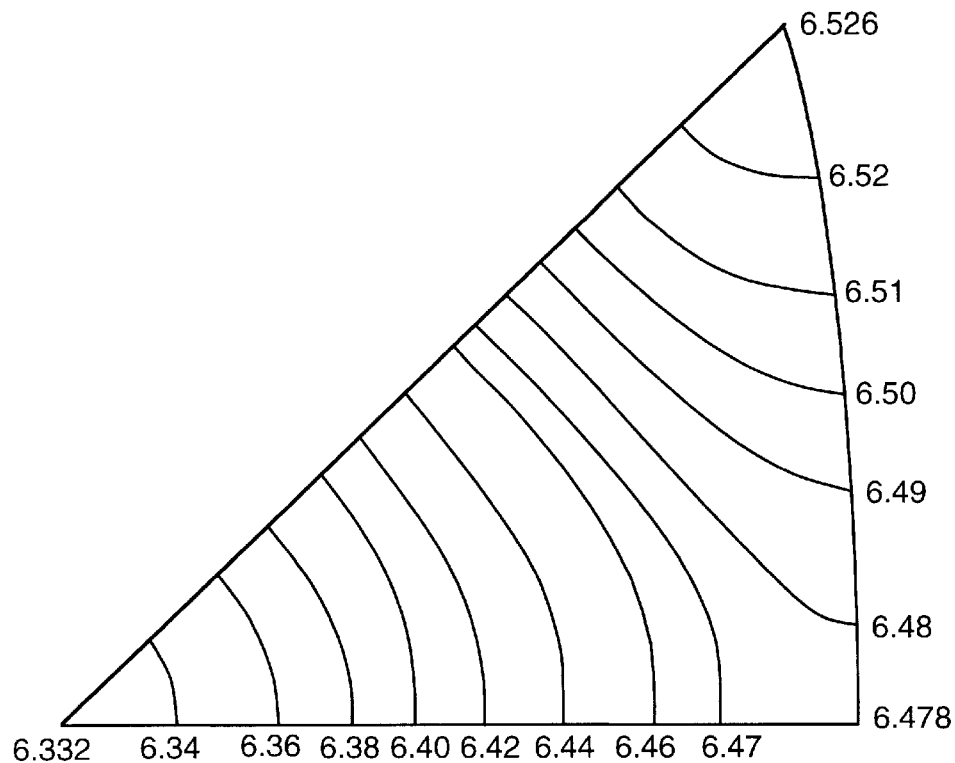
FIGS. 1a–1c are stereographic triangles which illustrate variations in wave velocity as a function of propagation direction.
Figure 1B:
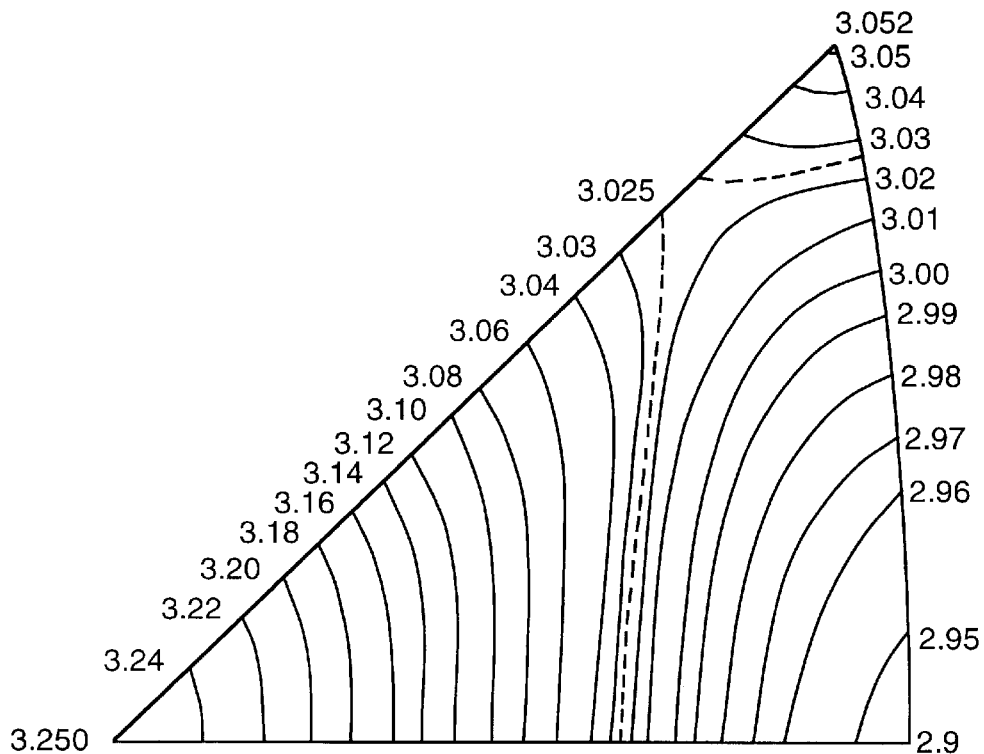
Figure 1C:
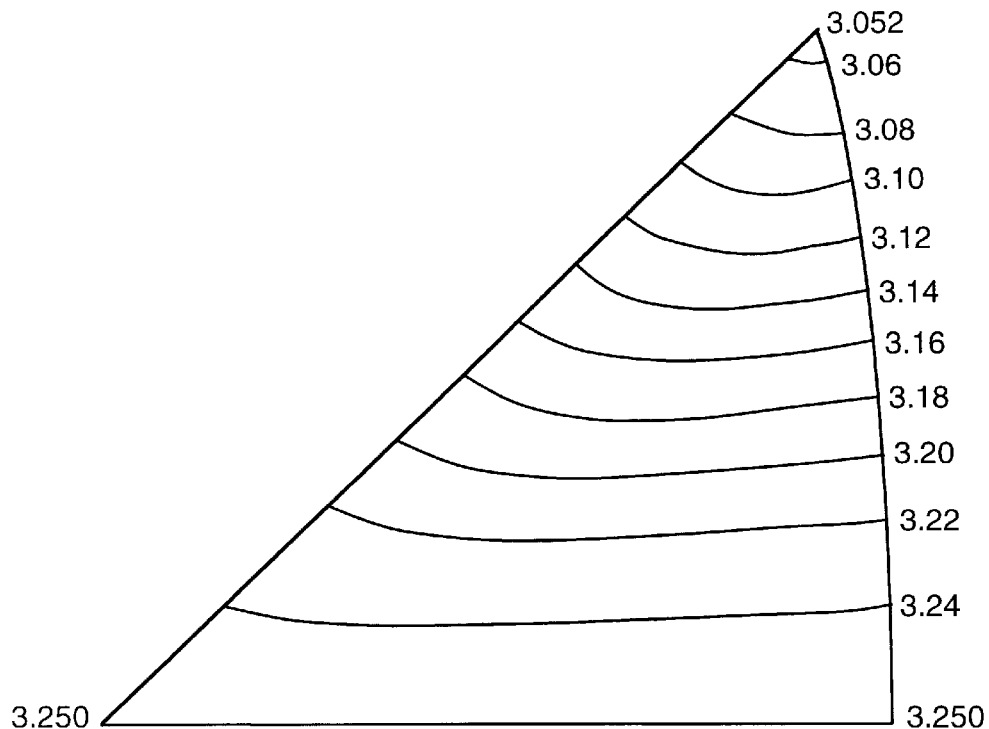

In an elastic medium, it is possible to propagate both longitudinal waves and transverse waves (also referred to as "shear waves"). In a longitudinal wave, the particle motion is parallel to the direction of propagation, whereas in a transverse wave, the particle motion is perpendicular to the direction of propagation.

The basic governing equation for elastic wave propagation in an anisotropic medium can be derived directly from the following equation of motion for a continuum(in the absence of body forces):

$$\rho \ddot{u}_i = \sigma_{ij,j} \quad (1)$$

where $\rho$ represents the density of the medium, $\ddot{u}_i$ represents the second derivative of the i-th component of the particle displacement with respect to time, and $\sigma_{ij,j}$ represents the partial derivative of the ij-th component of the second order stress tensor for the elastic solid with respect to the xj direction.

Under Hooke's law, the components of the stress tensor $\sigma$ at any point are a linear function of the components of the strain tensor $\epsilon$. This relationship is summarized in the following equation, which assumes a linearly elastic constitutive equation for the solid:

$$\sigma_{ij} = C_{ijkl} \epsilon_{kl} \quad (2)$$

Substituting equation (2) into equation (1) gives:

$$\sigma \ddot{u}_i = C_{ijkl} \epsilon_{kl,j} \quad (3)$$

For small displacements, in the case of a linear elastic anisotropic solid, the relationship between strain $\epsilon$ and displacement u is described by the equation:

$$\epsilon_{kl} = \frac{1}{2}(u_{k,l} + u_{l,k}) \quad (4)$$

where $u_{k,l}$ represents the partial derivative of $u_k$ with respect to $x_l$. Substituting equation (4) into equation (3) gives:

$$\rho \ddot{u}_i = \frac{1}{2}[C_{ijkl} u_{k,lj} + C_{ijkl} u_{l,kj}] \quad (5)$$

From symmetry, this reduces to the following equation:

$$\rho \ddot{u}_i = C_{ijkl} u_{k,lj} \quad (6)$$

For harmonic plane wave propagation in a given direction in the medium, the displacements can be represented by the following equation:

$$u_i = A_o \alpha_i e^{i[k(l_j x_j) - \omega]} \quad (7)$$

where $A_o$ is the displacement amplitude, $\alpha$ is the polarization vector which represents the direction of particle displacement, x is wave displacement, k is the wave number, l is the wave normal, and $\omega$ is the frequency.

Substituting the representation of equation (7) into equation (6) yields an eigenvalue problem which can be expressed as:

$$(C_{ijkl}l_jl_l - \rho V^2 \delta_{ik})\alpha_k = 0 \qquad (8)$$

where $\delta_{ik}$=the Kronecker delta and V=phase velocity.

Equation (8) is known as the Christoffel equation. The Christoffel equation describes the relationship between the velocity of a wave traveling through an elastic medium and the elastic properties (e.g. anisotropy) and orientation of the medium. The equation is a 3×3 equation in which the eigenvalues yield the velocities of wave propagation in a given direction, and the eigenvectors are the corresponding polarizations. The Christoffel equation can be used to describe the propagation of three waves (e.g., two transverse waves or "shear waves" and one longitudinal wave) through an elastic medium.

Figure 2:
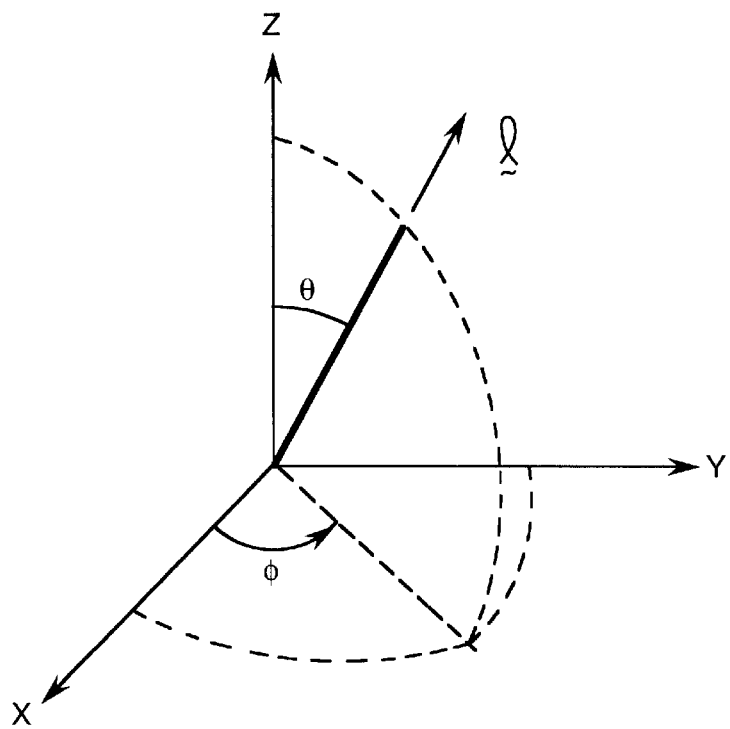
FIG. 2 shows the relationship between a wave normal vector and the axes of anistropy X, Y and Z.

By knowing the elastic properties of the medium and the direction of propagation (wave normal vector) relative to the axes of anisotropy (e.g. crystal axes), it is possible to calculate the velocity of the longitudinal and transverse waves in any direction. The elastic properties of the medium are represented in the Christoffel equation by the second order elastic constants $C_{ijkl}$ ("elastic moduli") which make up a "stiffness tensor" (also referred to as the "tensor of the elastic moduli"). An example of the elements which may be used to form the stiffness tensor $C_{ijkl}$ for a material having a cubic crystal structure are as follows:

$C_{11} = C_{22} = C_{33} = 35 \times 10^6 psi$ $C_{12} = C_{13} = C_{23} = 21.44 \times 10^6 psi$ $C_{44} = C_{55} = C_{66} = 18.46 \times 10^6 psi$ $\rho = 0.3125 \; lb./cu.in.$ The anisotropic orientation of the article relative to the wave normal vector can be defined by two orientation angles, $\phi$ and $\theta$. As shown in FIG. 2, $\phi$ and $\theta$ define the relationship between the anisotropic axes X, Y, and Z of the article, and the wave normal vector. The anisotropic axes X, Y, and Z represent the crystallographic axes in a crystal, for example, or other axes of anisotropy in an anisotropic material. The two orientation angles are related to the wave normal vector 1 by the following equation:

$$l = \begin{bmatrix} l_1 \\ l_2 \\ l_3 \end{bmatrix} = \begin{bmatrix} \sin\theta\cos\phi \\ \sin\theta\sin\phi \\ \cos\theta \end{bmatrix} \qquad (9)$$

With the foregoing equations, it is possible to compute three velocities for any wave normal direction relative to the axes of anisotropy (e.g. crystallographic axes), assuming that the elastic properties of the medium and the density of the medium are known. In an isotropic medium, the velocity of a longitudinal or transverse wave is independent of the propagation direction. By contrast, in an anisotropic medium, the wave velocity is dependent on the direction of propagation.

Figure 3:
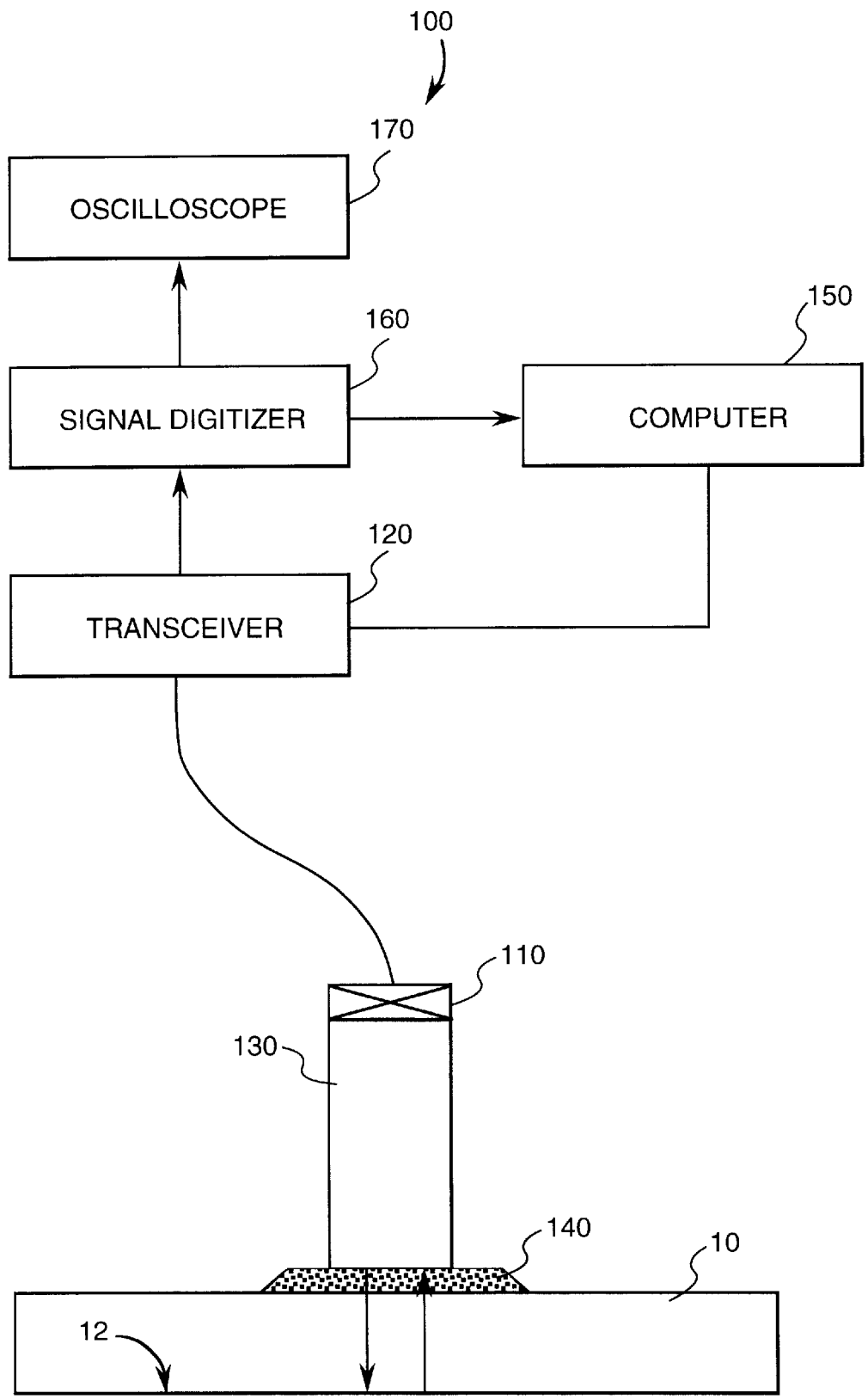
FIG. 3 illustrates a direct contact measurement apparatus according to an exemplary embodiment of the invention.

Exemplary embodiments of the invention provide an apparatus for determining an anisotropic orientation of a test medium based on measured transit times or velocities of waves propagated through the test medium. A schematic diagram of one embodiment of the invention is illustrated in FIG. 3. The apparatus 100 includes a transducer assembly 110, which generates waves in the test medium 10, connected to a transceiver 120, which is controlled by a computer 150. The transceiver 120 may be commanded by the computer 150 to produce an electrical signal which activates the transducer assembly 110 to generate a wave. The transducer assembly 110 also detects received waves, for example reflected ultrasonic waves, and generates electrical signals representative of the received waves, which are sent to the transceiver 120 where they are amplified for processing.

The transducer assembly 110 typically comprises a longitudinal transducer which generates longitudinal waves and a shear transducer which generates transverse waves. The polarization of the transverse wave generated by the shear transducer may be controlled by rotating the shear transducer about the wave normal. Preferably, both the longitudinal and shear transducers are piezoelectric transducers which generate ultrasonic waves, although other types of transducers may be used.

The transducer assembly 110 is typically directly coupled to the test medium 10 via a delay line 130 and a couplant 140. The delay line 130 is provided to improve the resolution between the transmitted and received waves, for example where the test medium is very thin, by increasing the period of time between the transmission of the transmitted signal and the reception of the reflected signal. The couplant is used to improve the efficiency with which the wave energy is transmitted into the test medium 10. The couplant is preferably a viscous fluid, for example PANAMETRICS Shear Wave Couplant or a viscous α-styrene resin, which is capable of supporting the propagation of transverse waves therethrough.

The amplified received signal output from the transceiver 120 may undergo conventional processing before it is received by the computer 150. For example, the amplified received signal, which is in analog form, may be sent to a signal digitizer 160 which digitizes the analog signal. The digital signal may then be transmitted both to an oscilloscope 170 for viewing, and to the computer 150 for execution of routines to analyze the received wave signals.

In operation, three waves may be propagated through the test medium 10 to the back surface 12 of the test medium 10 where they are reflected back to the transducer 110 through the couplant 140 and delay line 130. Samples of transmitted and reflected wave signals for longitudinal and transverse (shear) waves propagated through an anisotropic medium are shown in FIGS. 4a–4d.

Figure 4A:
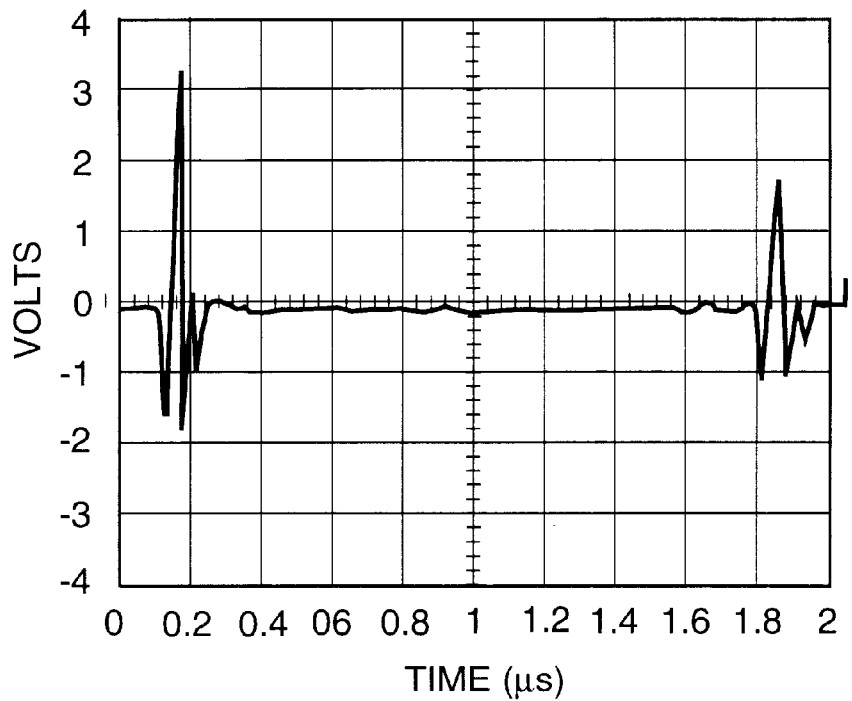
FIGS. 4a–4d illustrate examples of transmitted and reflected longitudinal and shear wave signals.
Figure 4B:
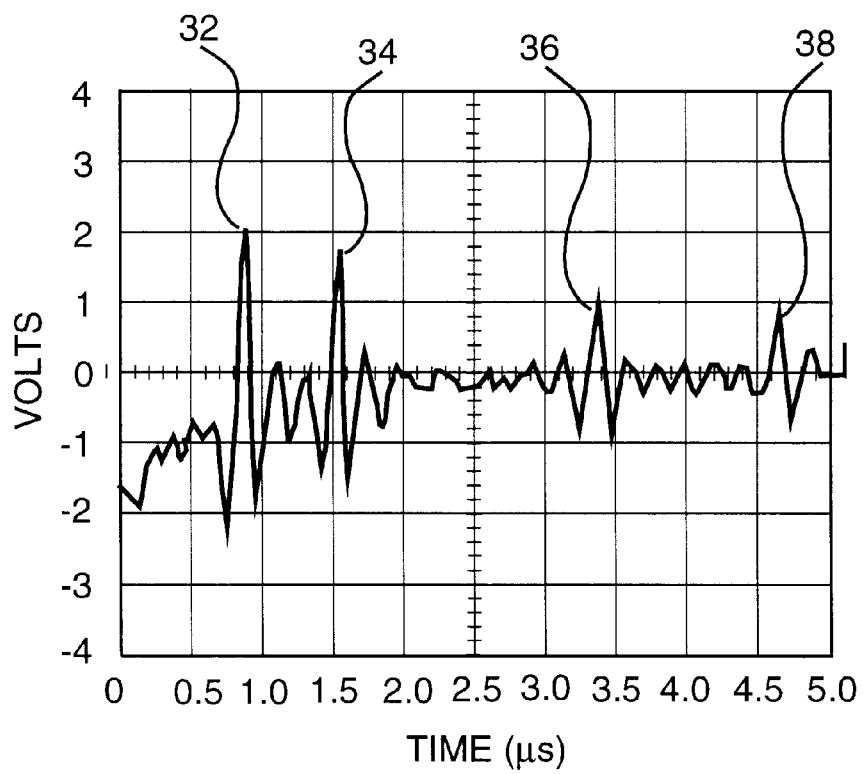
Figure 4C:
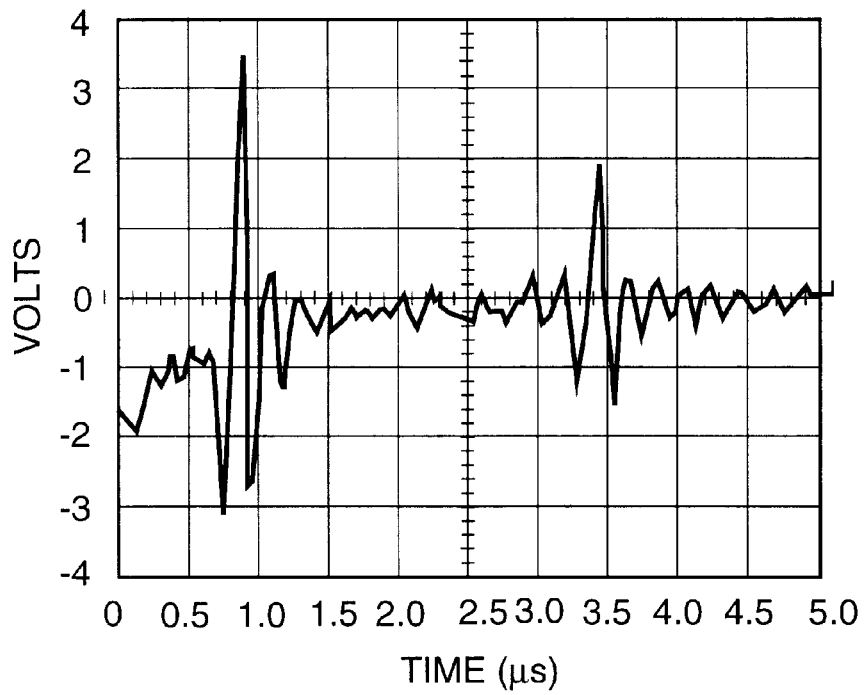
Figure 4D:
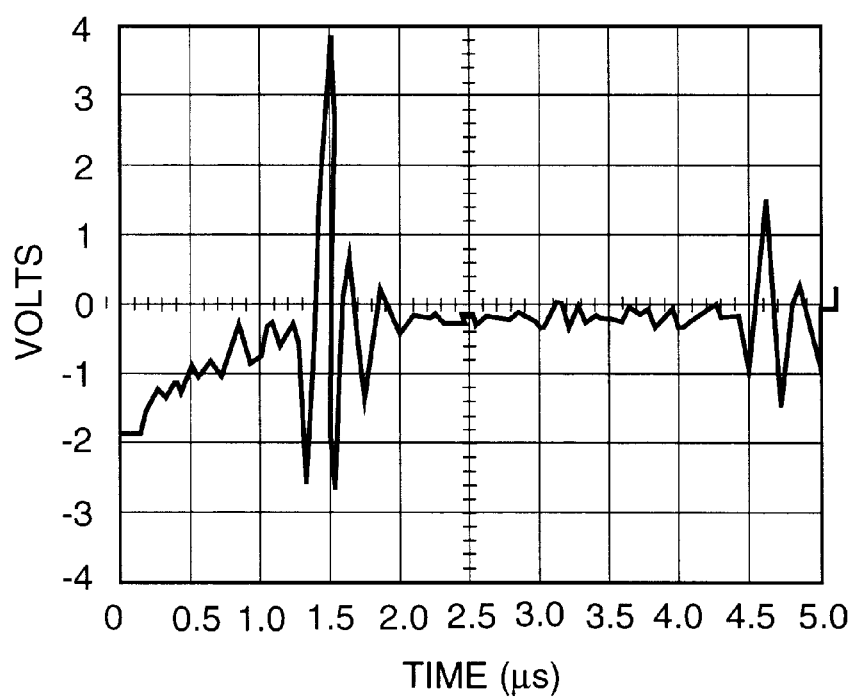

FIG. 4a illustrates transmitted and reflected wave signals for a longitudinal wave, FIG. 4c illustrates a first shear wave, and FIG. 4d illustrates a second shear wave. The shear waves in FIGS. 4c and 4d have different polarizations and velocities. The shear wave in FIG. 4c is referred to as a "fast shear wave" since its velocity is greater than that of the "slow shear wave" illustrated in FIG. 4d.

A single shear transducer may be used to propagate both fast and slow shear waves. Initially, the shear transducer may be coupled to the test medium 10 and rotated about the wave normal axis (transducer axis) to find the angle at which the amplitude of the fast shear wave is greatest. A measurement of the transmitted and reflected signals is shown, for example, in FIG. 4c. Because the fast and slow shear waves are orthogonal, the angle at which the amplitude of the slow shear wave is greatest is 90 degrees from that of the fast shear wave. Thus, by rotating the shear transducer 90 degrees about the wave normal, the slow shear wave having the largest amplitude is obtained, as shown in FIG. 4d. This method is advantageous, for example, when the reflection surface (i.e. the back surface of the test medium) is rough, because the amplitude of the transmitted fast and slow shear waves is greatest.

If the reflection surface is relatively smooth, both fast and slow shear waves may be obtained in a single measurement by choosing the angle of the shear transducer to be 45 degrees from the angles at which the amplitudes of the fast and slow shear waves are greatest. The shear transducer thus excites a fast shear wave 32 and a slow shear wave 34 in the test medium 10, and the reflected wave includes a first component 36 comprising a fast shear wave and a second component 38 comprising a slow shear wave, as shown in FIG. 4b.

The transit times for the three waves through the test medium 10 may be obtained by conventional methods of time measurement of the received digitized signals in the computer 150. The transit times are then used by the computer 150 to calculate the anisotropic orientation of the test medium, as will be described further below.

Figure 5:
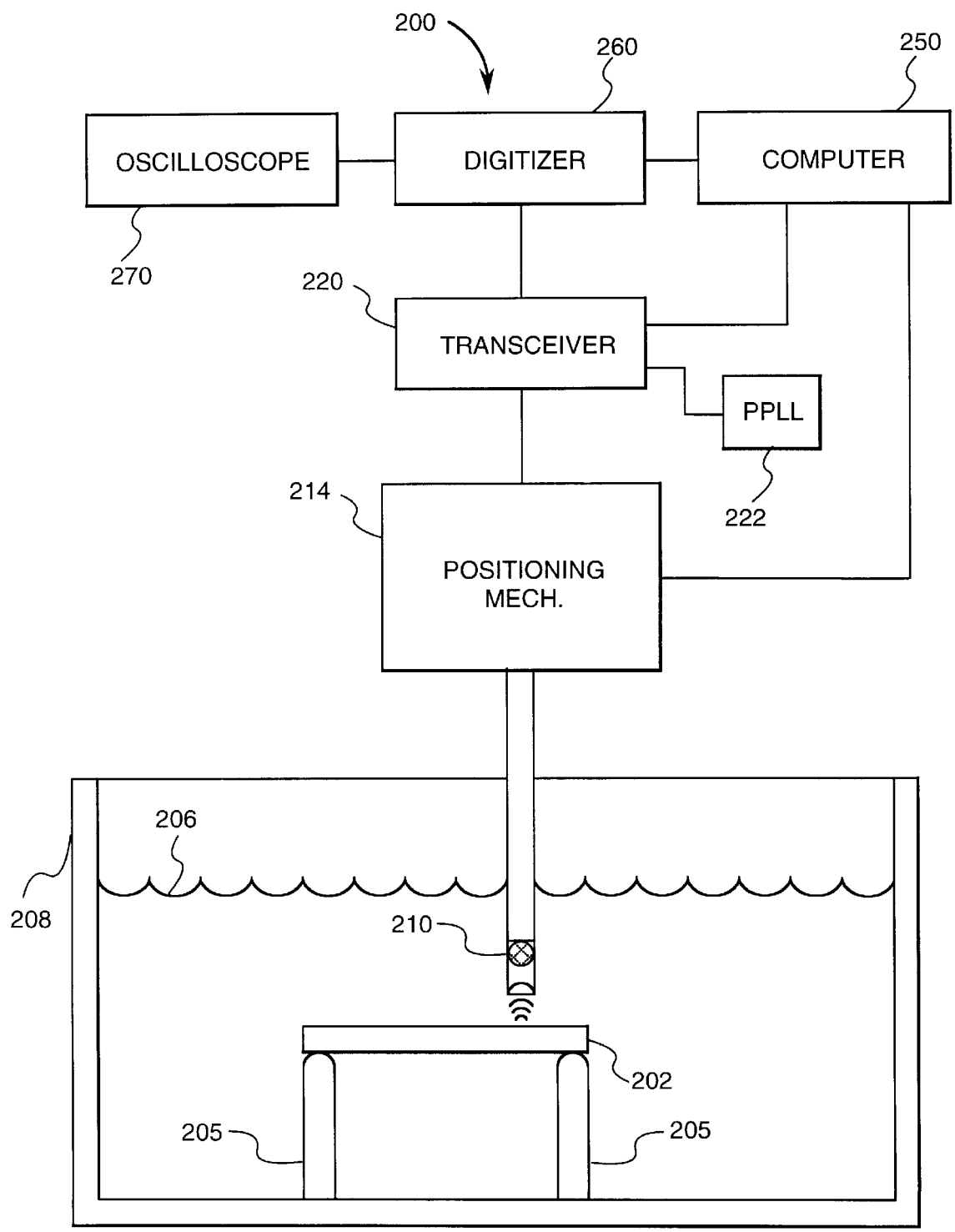
FIG. 5 illustrates a scanning apparatus according to an exemplary embodiment of the invention.

According to another embodiment of the invention, the propagation of waves through the test medium 10 can be facilitated by using an automated scanning apparatus, rather than a direct contact apparatus. As shown in FIG. 5, an exemplary scanning apparatus 200 includes transducer assembly 210 for transmitting and receiving waves which is mounted on a positioning mechanism 214. The transducer assembly typically comprises a spherical transducer which generates a focused ultrasonic beam which is focused at a point on the surface of the test medium 202, for example. The spherical transducer may be a transducer comprising a spherically curved element or a flat element focused by a spherical acoustic lens, for example. The transducer assembly may also comprise an electromagnetic acoustic transducer (EMAT) which generates ultrasonic waves, as well as other types of known transducers.

An EMAT produces ultrasonic waves in conducting materials by producing high frequency electromagnetically induced stains in the material. EMATs have the advantages of being non-contact so that no couplant is necessary, and operating at high temperatures, if desired. EMATs can generate bulk waves, either longitudinal or shear, with known polarization, and are particularly useful for ferromagnetic materials.

The transducer assembly 210 and the test medium 202 may be immersed in a fluid 206 such as water which is contained in a tank 208. The fluid 206 serves as a couplant through which the waves generated by the transducer assembly 210 propagate en route to the test medium 202. The transducer assembly 210 may be moved freely in the fluid 206, therefore, while maintaining acoustic communication with the test medium 202. The test medium is typically supported by supports 205.

The positioning mechanism 214 is used to position the transducer assembly 210 with respect to the article 202 to be tested. Preferably, the positioning mechanism 214 includes translation bearings which allow the transducer assembly 210 to move in three degrees of translational freedom. In addition, the positioning mechanism 214 preferably includes rotation bearings which allow the transducer assembly 210 to be rotated about gimbal and swivel rotary axes. Suitable conventional motors may be provided to control the translational and rotational movement of the transducer assembly 210 relative to the test medium 202.

Generally, the fluid 206 in the tank 208 is a relatively non-viscous fluid which supports longitudinal wave propagation but not transverse wave propagation. To generate transverse waves in the test medium 202, the phenomenon of mode conversion may be utilized. Mode conversion refers to the well known phenomenon that a longitudinal wave incident on an elastic solid will generate other wave modes, e.g. transverse waves, depending upon the angle of incidence of the incident longitudinal wave. For example, a focused conical beam containing a range of incident angles and having an axis of beam symmetry perpendicular to the surface of the test medium will generate a transmitted longitudinal wave, and two transmitted shear waves (fast and slow) having orthogonal polarizations in the test medium. This phenomenon, which is described for example in R. S. Gilmore, *Industrial Ultrasonic Imaging and Microscopy*, 29 J. Phys. D: Appl. Phys. 1389 (1996), is useful for generating transverse waves in the test medium 202 where the coupling fluid does not support transverse waves.

The process of gathering data at particular points on the test medium can be automated with a computer 250. The computer 250 may be programmed to transmit command signals to the rotational and translational motors of the positioning mechanism 214 to position the transducer assembly 210 at a desired position and orientation. The computer 250 may also be programmed to command a transceiver 220 to generate a signal to activate the transducer assembly 210 at desired times.

As in the direct contact embodiment illustrated in FIG. 3, the scanning apparatus 200 includes a digitizer 260 which digitizes received signals from the transceiver 220 and transmits the digitized signal to an oscilloscope 270 for viewing, and to the computer 250 for execution of routines to analyze the received signals.

Figure 6:
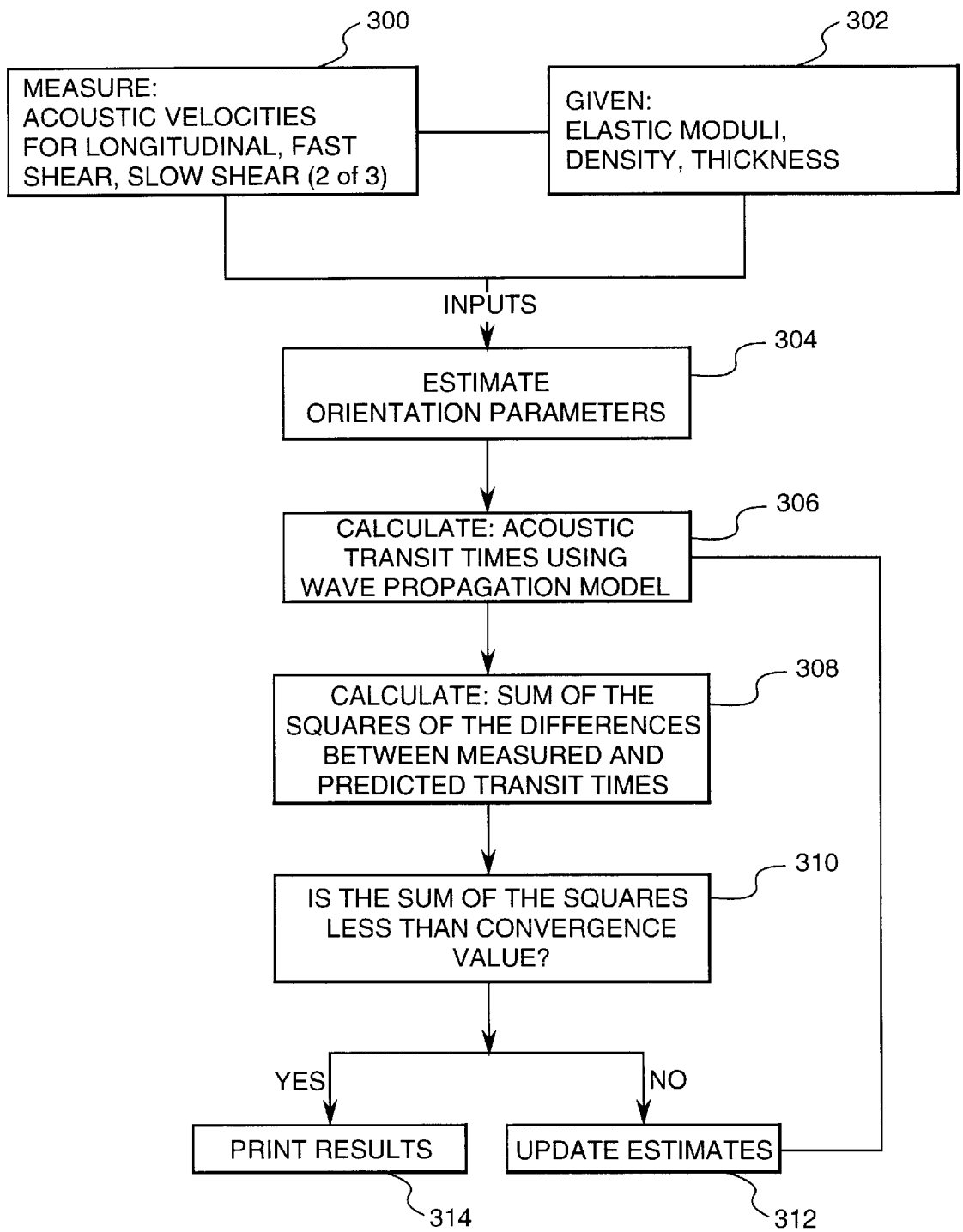
FIG. 6 is a flowchart describing a method according to an exemplary embodiment of the invention.

In both the direct contact embodiment of FIG. 3 and the scanning apparatus embodiment of FIG. 5, the computer may be programmed to execute a method for determining a crystal orientation of the test medium based on the measured wave transit times or velocities. According to a first exemplary method as illustrated in the flowchart of FIG. 6, transit times are measured for two of the three waves (e.g., one longitudinal wave, one transverse wave) and input to the computer at step 300, along with the stiffness matrix for the test medium, the density of the test medium, and the thickness of the test medium in step 302. At step 304, an initial estimate of the angles $\theta$ and $\phi$ (FIG. 2) which define the crystal or anisotropic orientation with respect to the wave normal is input by the user.

At step 306, the values from steps 302 and 304, i.e., stiffness matrix, density, thickness, and estimated orientation, are substituted into the Christoffel equation to calculate a predicted transit time for the two of three waves. At step 308, the differences between the measured and predicted transit times are obtained, and these values are squared and then summed. The sum of the squares is compared at step 310 to a predetermined convergence value. If the sum of the squares is greater than the predetermined convergence value, the estimates for the angles $\theta$ and $\phi$ which specify the crystal orientation are updated at step 312.

The estimates for the orientation angles may be updated with a routine such as the well known-Marquart approach with a numerical Jacobian. Reference is made, for example, to Kenneth Levenberg, *A Method for the Solution of Certain Non-linear Problems in Least Squares*, 2 Quarterly of Applied Mathematics 164–168 (1944); Donald W. Marquardt, *An Algorithm for Least-squares Estimation of Nonlinear Parameters*, 11 SIAM Journal on Applied Mathematics 431–441 (1963); and IMSL Inc., *FORTRAN Subroutines for Mathematical Applications User's Manual*, §8.1.3 p. 1023–1029 (1991). The reconstruction process is an iterative search to find the best match between predicted and measured acoustic transit times for each of the measured acoustic rays. Other known iterative routines may be used to update the estimates for the orientation angles, for example the Newton-Raphson method or the gradient method (also known as "the method of steepest descent").

After the orientation angle estimates are updated, flow returns to step 306 where the Christoffel equation is again invoked to calculate predicted transit times for the two waves based on the updated estimates for the orientation angles. Step 308 is then repeated.

If the sum of the squares of the difference between the measured and predicted transit times of the waves is found in step 310 to be less than the predetermined convergence value, convergence is achieved in step 314, and the predicted orientation angles are taken to be the actual orientation angles.

Figure 7:
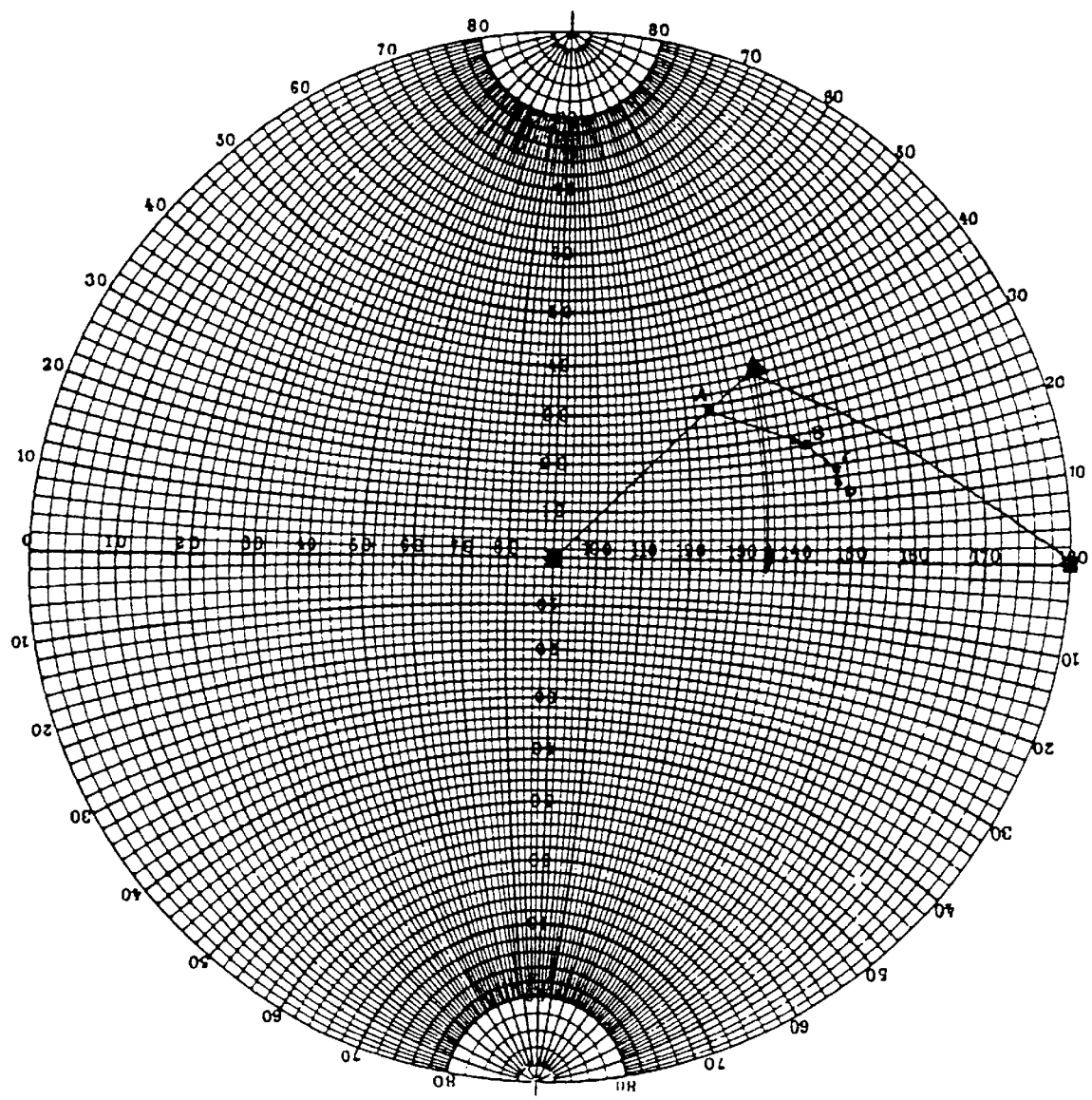
FIGS. 7–9 illustrate the method of FIG. 6 on a stereographic plot.

The iteration process can be conveniently illustrated on a stereographic plot, such as that shown in FIG. 7. The stereographic plot of FIG. 7 represents possible combinations of two angles, for example $\theta$ and $\phi$, and can thus be used to represent the crystal orientation of a test medium with respect to the propagation direction of a wave. In FIG. 7, $\phi$ is defined on the horizontal axis, and $\theta$ is defined on the vertical axis.

Figure 8:
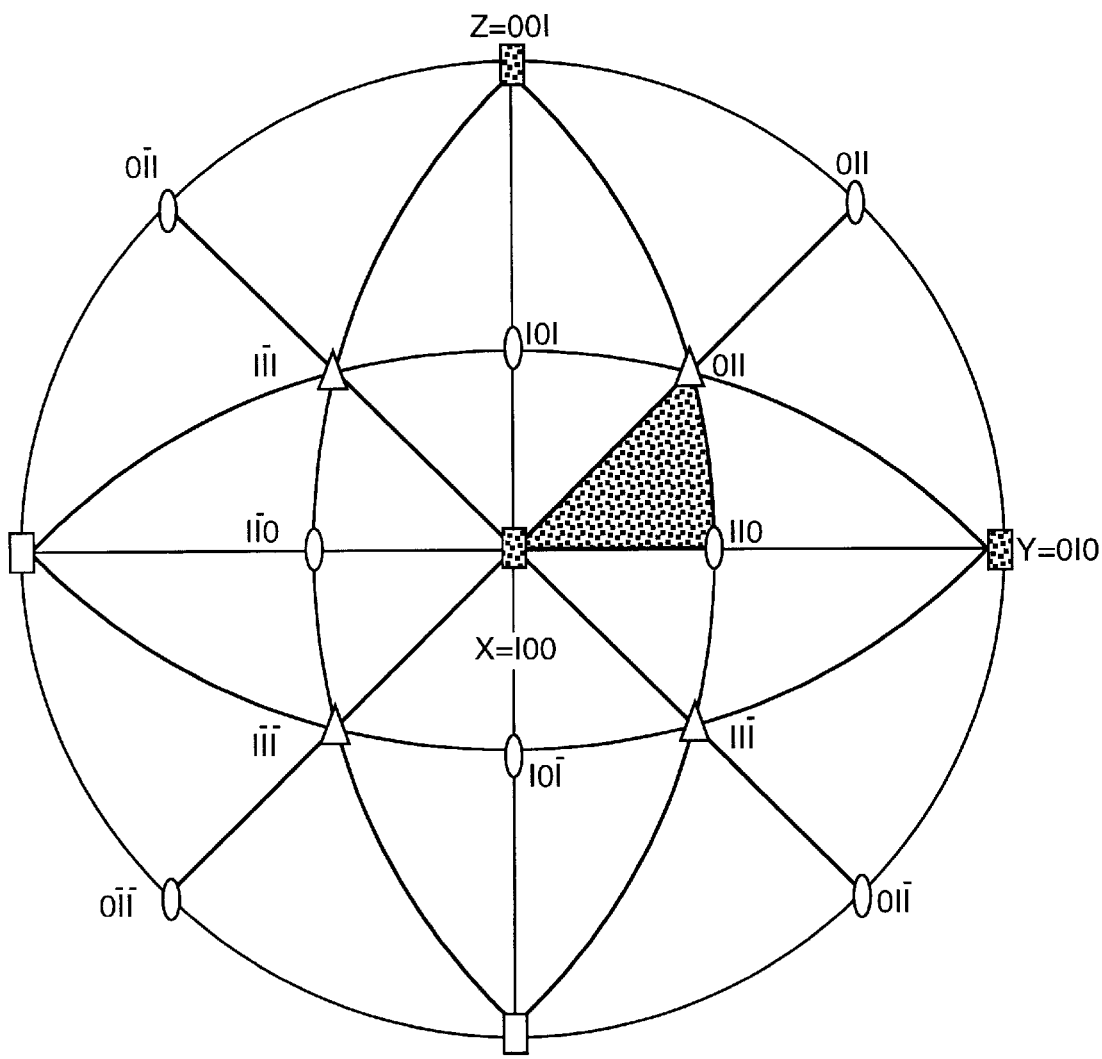

The stereographic plot of FIG. 7 can be divided into a number of stereographic triangles, each triangle representing a range of values of the angles $\theta$ and $\phi$. FIG. 8, for example, shows a stereographic plot divided into 24 stereographic triangles. Each stereographic triangle is defined by three vectors at the corners of the stereographic triangle which define a range of values for $\theta$ and $\phi$.

Figure 9:
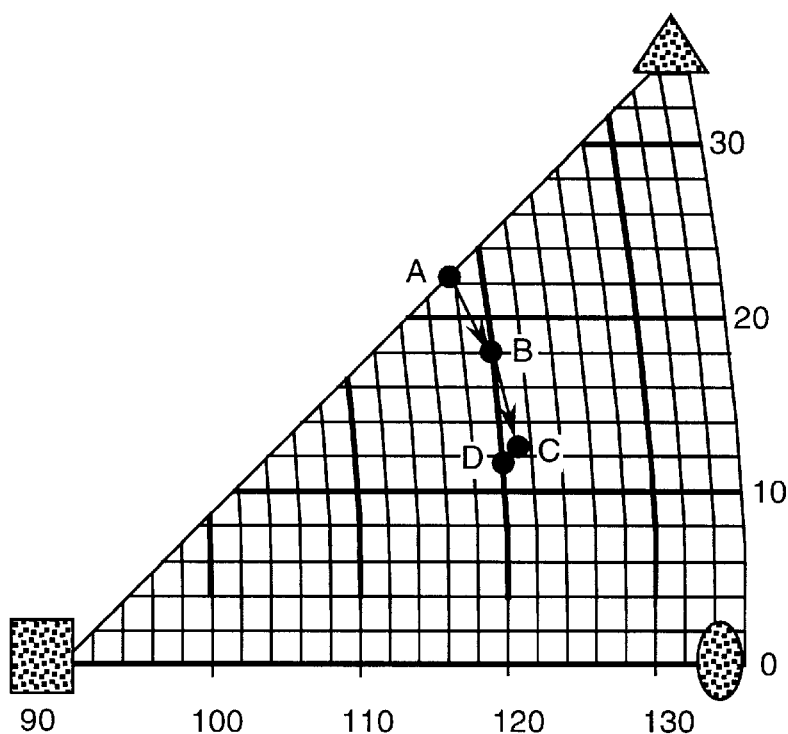

FIG. 9 illustrates graphically an example of an iteration to determine the crystal orientation angles $\theta$ and $\phi$ based on actual measurements of wave transit time in a test medium. As shown at point A in FIG. 9, the initial estimate for $\theta$ was 23 degrees, and the initial estimate for $\phi$ was 115 degrees. These initial estimates were used in step 306 to calculate predicted wave transit times for each wave mode. In step 310, the predicted transit times were found not to be close enough to the measured transit times for convergence to occur, thus the estimates for $\theta$ and $\phi$ were updated at step 312, indicated at point B in FIG. 9. After two more iterations, indicated by points C and D, convergence was achieved in step 314.

FIG. 7 illustrates a second iteration history in which a different initial estimate of the orientation angles $\theta$ and $\phi$ was used. As shown in FIG. 7, the final values for $\theta$ and $\phi$ were found to be located in a stereographic triangle which is different from the stereographic triangle of FIG. 9. This result is due to the symmetry of the particular test medium used, which was a nickel-based superalloy with a cubic crystal structure. The cubic crystal structure results in 24 equivalent combinations of $\theta$ and $\phi$ for any particular crystal orientation, each equivalent combination being located in one of the 24 equivalent stereographic triangles of FIG. 8. Therefore, depending on the initial estimate provided in step 304, a different one of the 24 equivalent orientations may be obtained. The method, however, will converge to one of the 24 equivalent orientations in one of the 24 stereographic triangles, and the thickness will be accurate regardless of which stereographic triangle is selected. Similar results are obtained for other symmetrical media, such as hexagonal crystals.

In the exemplary method of FIG. 6, two of the three possible wave transit times are input at step 300. Because only two wave transit times (e.g. one longitudinal, one transverse) are needed, the transit time for the additional wave (e.g. transverse) can be used to refine the method. For example, in step 300, three as opposed to two wave velocities can be measured, so that in step 312, the estimates for the two orientation angles are updated based on three measured wave transit times, rather than two, which provide greater accuracy.

Figure 10:
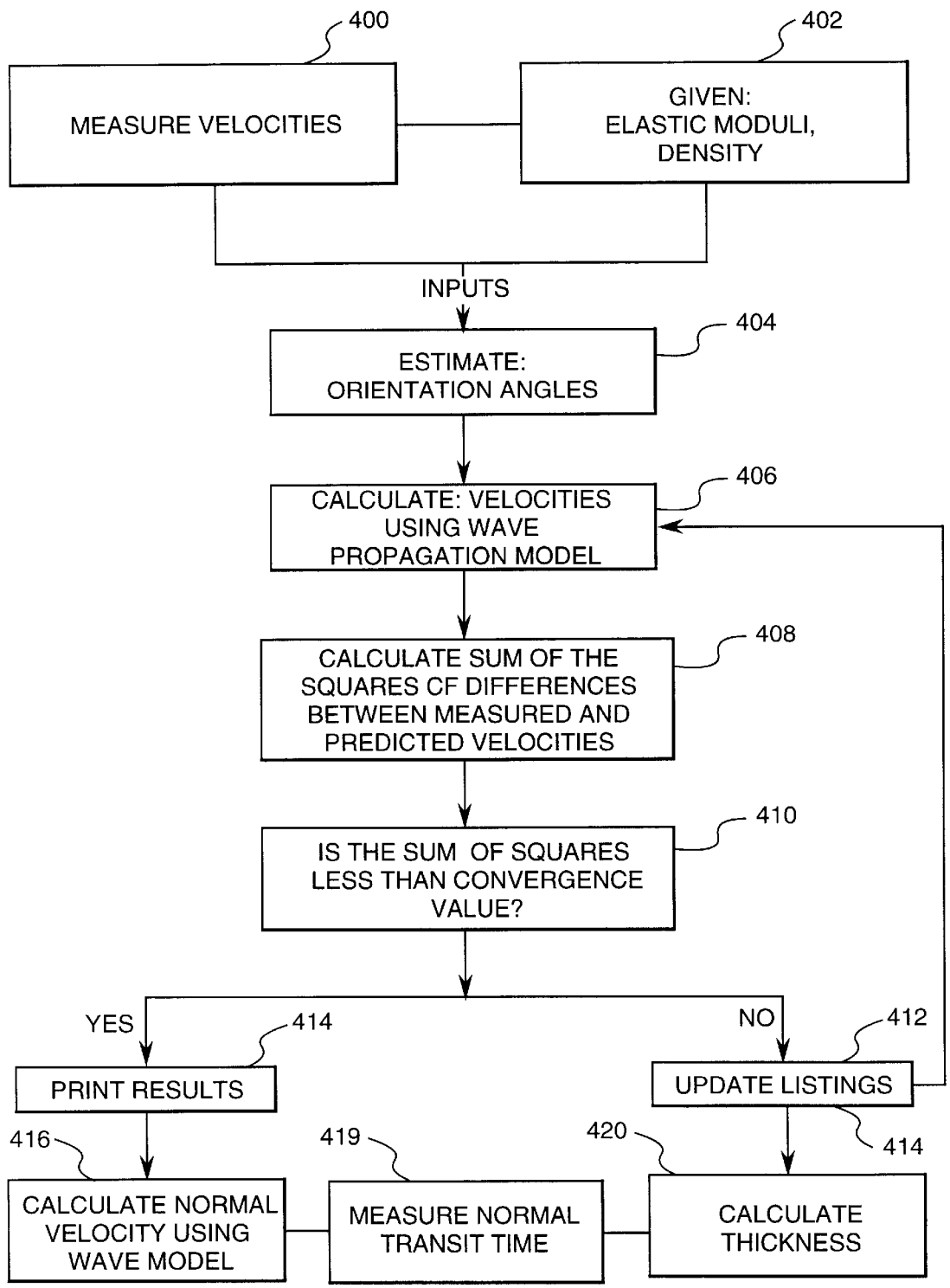
FIG. 10 illustrates a method according to another embodiment of the invention.

In the method shown in FIG. 6, a measured thickness of the test medium is input at step 302. The thickness of the test medium may be directly measured using any conventional measurement device. If it is not possible to directly measure the thickness, several alternative methods are provided. In general, these methods involve the steps of determining wave velocities of two of the three modes of interest, deducing crystal orientation with the Christoffel equation based on the wave velocities, and obtaining a thickness based on measuring a transit time of a wave of known velocity propagated normal to the surface of the test medium. These steps are illustrated as steps 400, 414, and 420 in the flowchart of FIG. 10.

According to a first method for determining wave velocity (step 400), the wave velocity is obtained by measuring the transmission and reflection coefficients for each wave mode at an interface between the test medium and a "transmission medium" of known acoustic impedance. The acoustic impedance is defined as the density of the transmission medium times the wave velocity through the transmission medium. The reflection and transmission coefficients at normal incidence are known to be related to the densities and phase velocities of the two media on opposite sides of the interface by the following equations:

$$R = \frac{A_r}{A_i} = \frac{\rho_2 v_2 - \rho_1 v_1}{\rho_2 v_2 + \rho_1 v_1}, T = \frac{A_t}{A_i} = \frac{2\rho_1 v_1}{\rho_2 v_2 + \rho_1 v_1} \quad (10)$$

where "A"=wave amplitude, $\rho$=density, "v"=velocity, and the subscript "i"=incident wave, "r"=reflected wave, "t"= transmitted wave, "1"=transmission medium, and "2"= reflecting medium (i.e. the test medium 10). The transmission medium may simply comprise water surrounding the test medium. Alternatively, the transmission medium may comprise a buffer rod.

Preferably, the reflected wave amplitude $A_r$ and the transmitted wave amplitude $A_t$ are measured, since it is more difficult to measure the incident wave amplitude $A_i$ accurately. The reflected wave amplitude $A_r$ and the transmitted wave amplitude $A_t$ are received by a suitable transducer, for example the transducer which propagates the waves through the transmission medium to the interface. The ratio of $A_r$ to $A_t$ is then calculated by the computer to eliminate the additional unknown, $A_i$. Because the density and wave velocity of the transmission medium are known, and the density of the test medium is known, the unknown velocity through the test medium can be calculated for each mode of interest, longitudinal and transverse, without knowledge of the thickness.

According to another exemplary method for measuring wave velocity through the test medium, the test medium is immersed in water to determine the critical angle of reflection of a given mode. Snell's Law may then be used to determine the velocity since the velocity in water is known and the angles of the transmitted and refracted waves are known:

$$\frac{\sin\theta_{incident}}{V_{water}} = \frac{\sin\theta_{refracted}}{V_{refracted}} \quad (11)$$

According to a third exemplary method for determining the velocity of a wave propagated through the test medium, guided waves, e.g. plate waves or surface waves, are propagated across a surface of the test medium for a predetermined distance to measure wave speed.

The three above described methods (i.e., determination of reflection and transmission coefficients, critical angle, or surface wave velocity) may be used to obtain the velocities of longitudinal and transverse waves propagating in the test medium. This is represented as step 400 in FIG. 10. After the velocities have been measured, and the density and stiffness matrix have been input at step 402, the orientation angles θ and φ are estimated at step 404. Next, the wave propagation model, i.e, the Christoffel equation, is used to calculate predicted velocities based on the estimated crystal orientation angles, the stiffness matrix, and the density. In step 408, the differences between the predicted and measured velocities are calculated and summed. If the sum of the squares is greater than the predetermined convergence value as determined in step 410, the estimated orientation angles are updated in step 412, and flow returns to step 406. If the sum of the squares is less than a predetermined convergence value, the estimated orientation angle values are taken to be the actual orientation angle values in step 414.

After the orientation angles are obtained in step 414, the velocity normal to the surface of the test medium is calculated in step 416 with the Christoffel equation, for each wave mode. A wave is then propagated normal to the surface of the test medium to measure a transit time of the wave in step 418. Finally, the thickness is obtained in step 420 by multiplying the wave velocity by the transit time. Thus, the crystal orientation and thickness of a test medium can be obtained when it is not possible to directly measure the thickness.

In many applications in which the thickness is not known, it may be burdensome to carry out a separate step for determining the thickness of the test medium for each point at which the anistropic orientation is measured. For example, it may be cumbersome to calculate transmission and reflection coefficients by measuring transmitted and reflected wave amplitudes at each point in question in addition to measuring transit times for thickness. According to another embodiment of the invention, the anistropic orientation and thickness of a test medium can be determined simultaneously.

Figure 11:
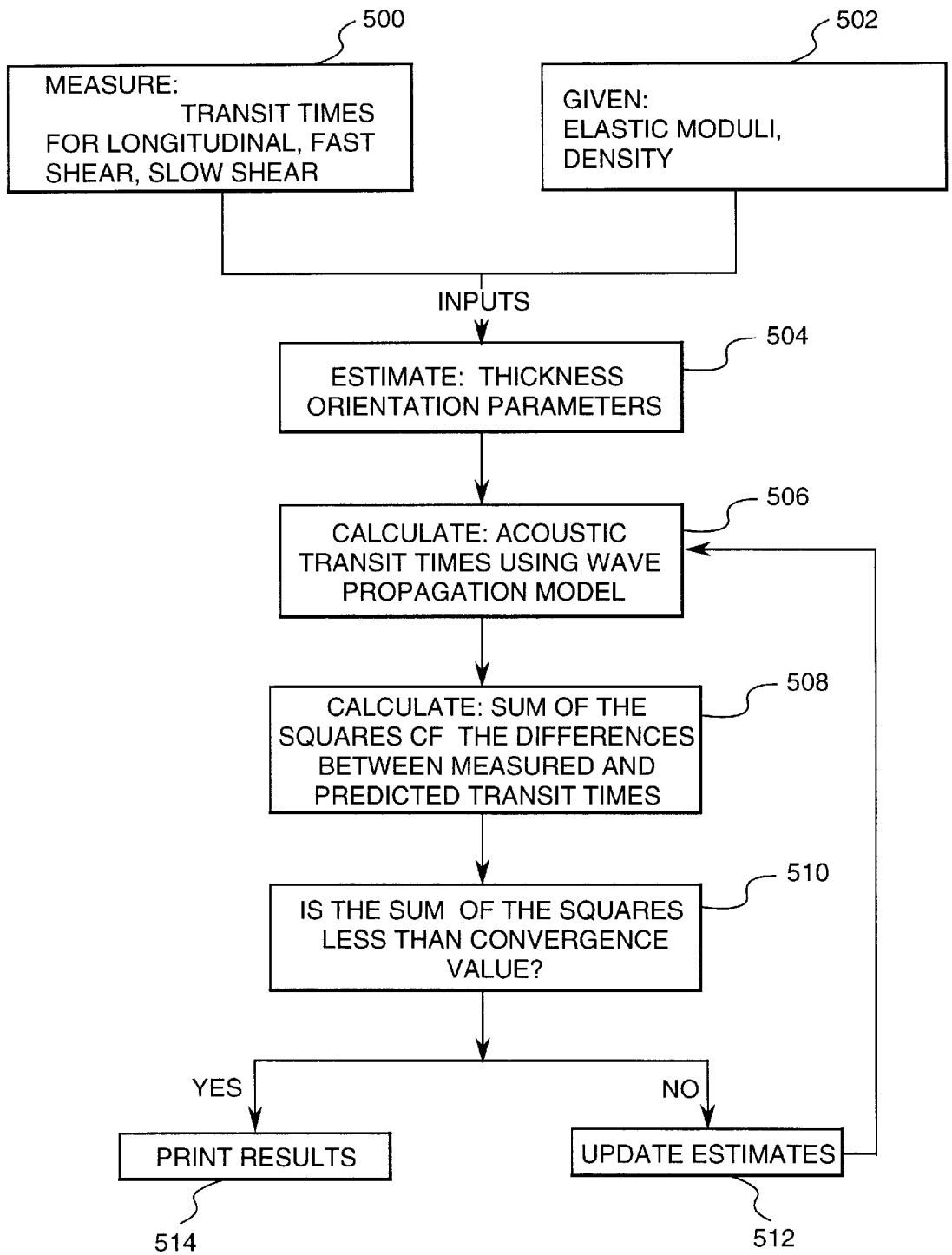
FIG. 11 illustrates a method according to a further embodiment of the invention.

The method according to this embodiment incorporates three wave transit time measurements and a least squares minimization routine to simultaneously determine three unknown parameters, θ, φ, and thickness. As shown in FIG. 11, step 500 involves measuring transit times for three waves (e.g. longitudinal, fast shear, slow shear) propagated through the test medium. The additional measurement is obtained because both the thickness and the two orientation angles θ and φ are unknown. These waves can be generated by the direct contact apparatus shown in FIG. 3 with longitudinal and shear transducers, or by the scanning apparatus shown in FIG. 5 through mode conversion. In step 502, the elastic constants, i.e. stiffness matrix $C_{ijkl}$, and density of the test medium are input.

At step 504, estimates for both the thickness and the orientation angles θ and φ are input. The estimated thickness and orientation angles are substituted into the Christoffel equation in step 506 to yield predicted wave transit times for the longitudinal, fast shear, and slow shear waves. In step 508, the differences between the predicted and measured wave transit times are calculated and squared and summed. The sum of the squares is then compared to a predetermined convergence value in step 510. If the sum of the squares is less than the predetermined convergence value, the current values for thickness and orientation angles are taken to be the actual values in step 514. Conversely, if the sum of the squares is greater than the predetermined convergence value, the estimates for the thickness and orientation angles are updated in step 512. The estimates for thickness and anisotropic orientation are preferably updated using the Levenberg-Marquardt approach with a numerical Jacobian, as described above.

To further expedite the process of gathering data at different points on a test medium, the scanning apparatus 200 shown in FIG. 5 can be implemented to move the transducer 210 from point to point on the test medium 202 in a controlled manner and to generate and detect the desired waves at each point. The scanning apparatus 200 is particularly useful in applications in which relative velocity measurements are acceptable. For example, scanning to determine relative velocities may be desirable in large parts if an accurate initial velocity measurement can be made.

The accuracy of the relative velocity measurements may be enhanced by using an automatic frequency control, such as a pulse phase locked loop (PPLL) 222, to accurately track changes from point to point on a test medium 202. For example, the frequency of the transducer can be adjusted so that the echo overlaps with the incident wave within the test medium 202. The interference between the echo and the incident wave produces a series of maxima and minima corresponding to constructive and destructive interference. By varying the frequency of the transducer the interference pattern will be changed and the velocity obtained from:

$$\frac{\Delta v}{v} = \frac{\Delta f}{f} \tag{12}$$

where Δf=the frequency separation between adjacent frequencies producing the same interference pattern and Δv=the change in velocity.

For scanning purposes, the frequency can be set so that the echo and incident wave destructively interfere to yield a null. By carefully tracking the change in frequency with a pulse phase locked loop to maintain the null, it is possible to obtain an accurate measurement of the change in velocity from point to point.

The accuracy of the above described methods can be further increased by obtaining additional measurements, i.e. oversampling, to create an overdetermined system. For example, at a particular test point, an additional group of longitudinal and transverse waves can be propagated in a different direction to obtain additional measurements. The thickness and orientation angles θ and φ are then updated based on six transit time measurements, rather than three, which improves the accuracy of the results.

Figure 12A:
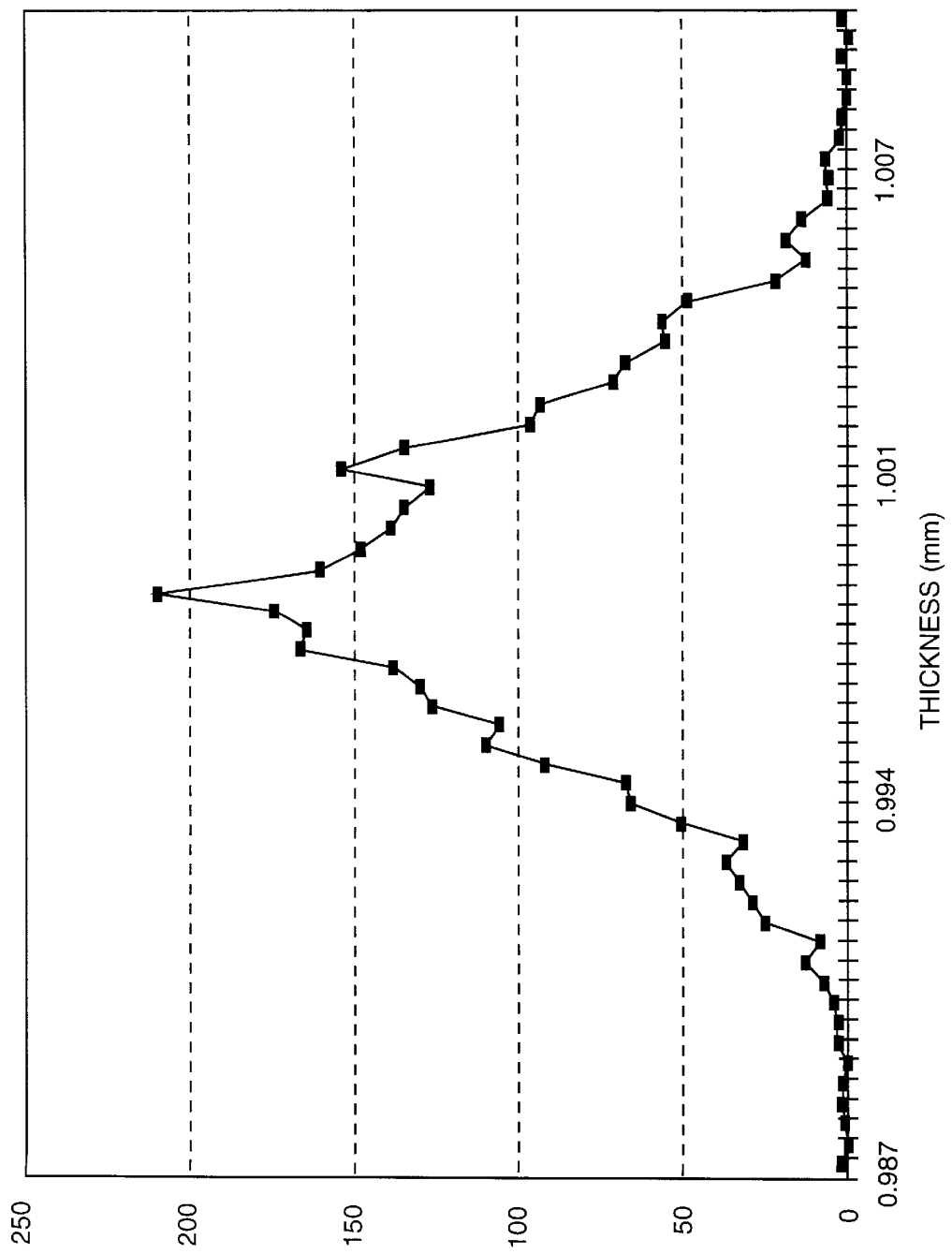
FIGS. 12a–12c are histogram plots of thickness and orientation measurements made with the method of FIG. 11.
Figure 12B:
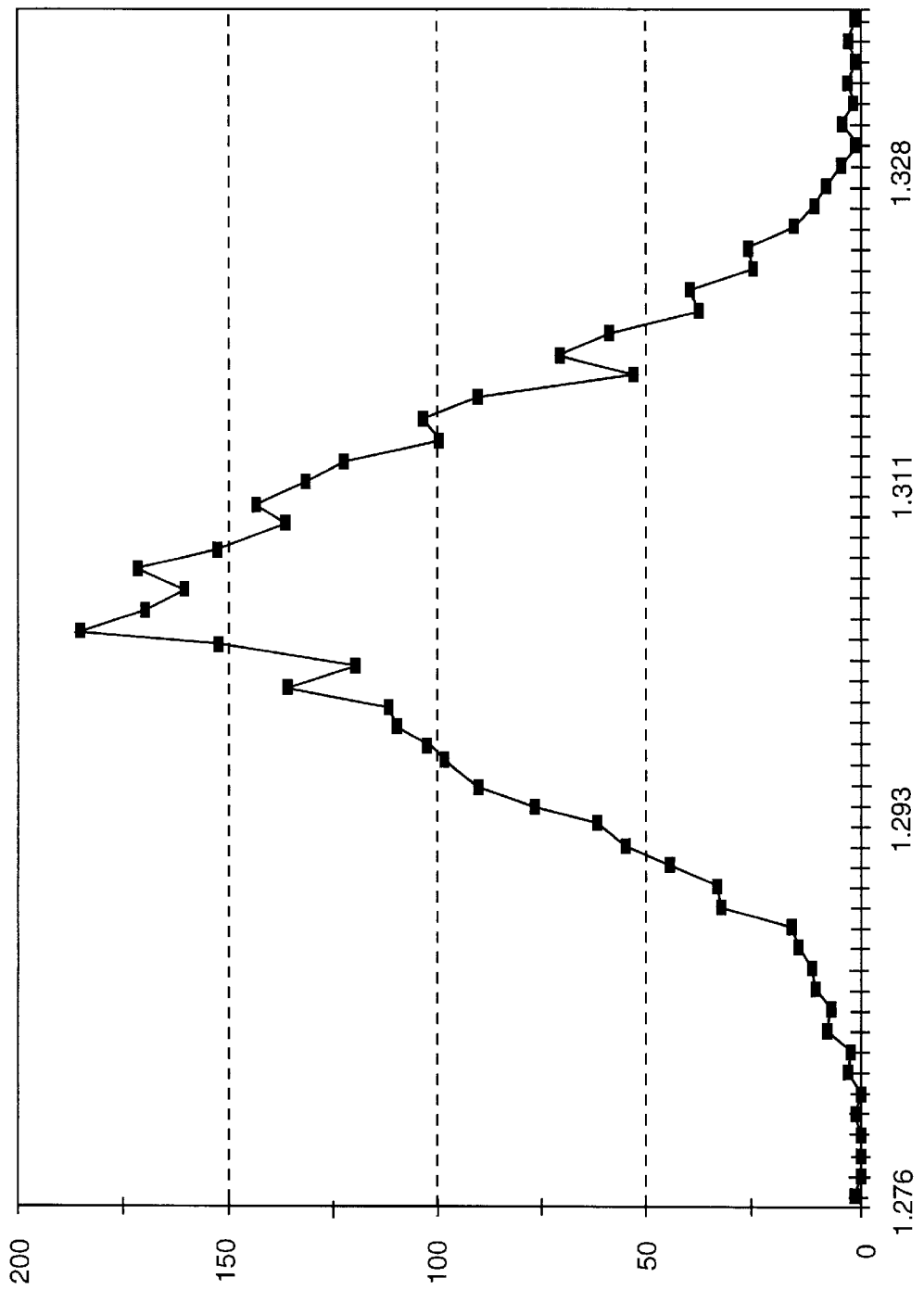
Figure 12C:
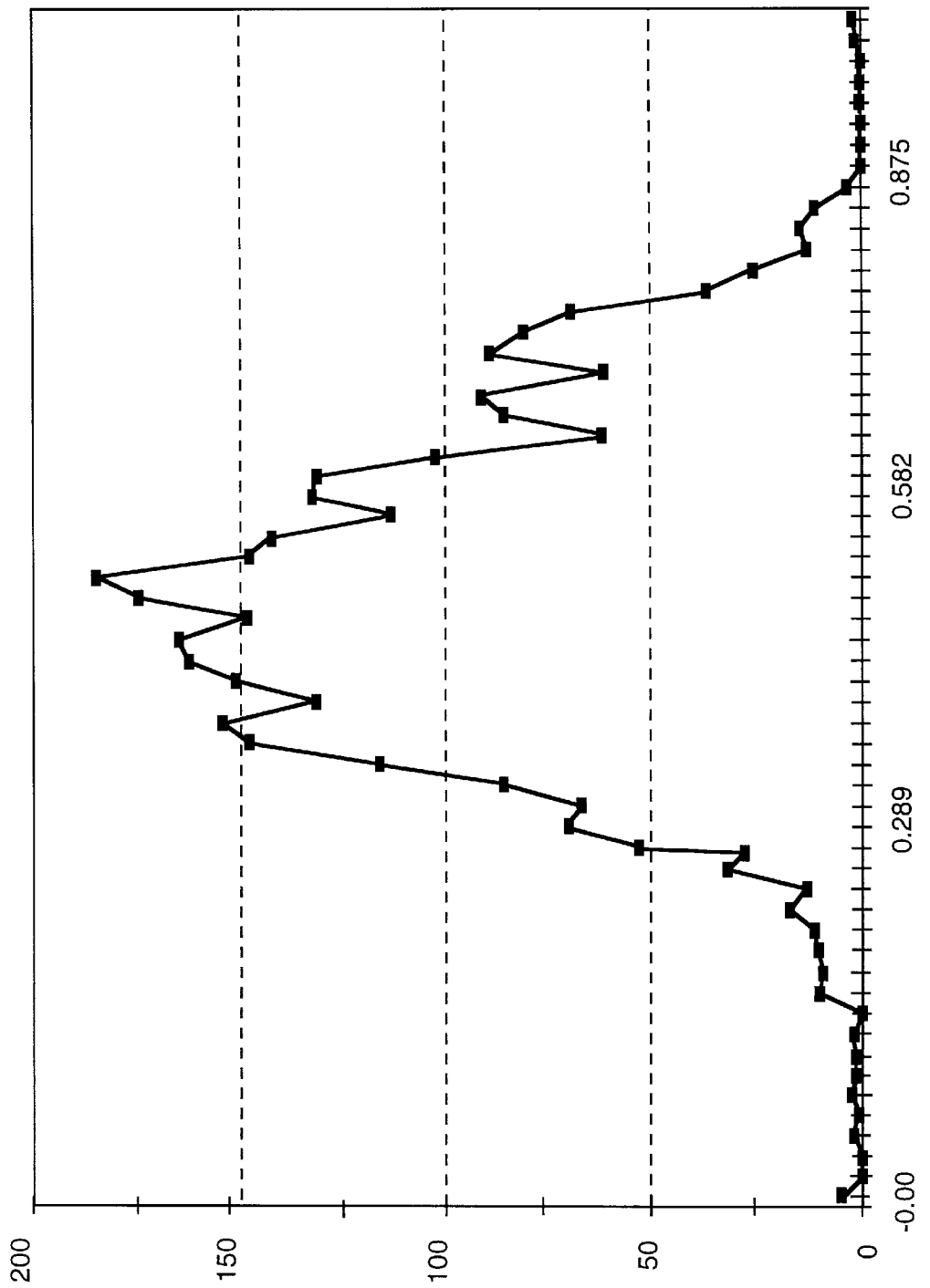

To evaluate the effectiveness of the above-described method, a series of 3,000 tests were run with synthetic data to simulate experimental error. The synthetic transit time measurements were distributed in a Gaussian distribution with a standard deviation of 2.5%. The actual and reconstructed values are shown in the table below, and histogram plots of the 3000 reconstructed values are shown in FIG. 12*a* (thickness in mm), FIG. 12*b* (φ in radians), and FIG. 12*c* (θ in radians).

| Parameter | Actual | Reconstructed (ave) | Std. Deviation |
|---|---|---|---|
| thickness | 1.0000 mm | 1.00004 | 0.00330 |
| φ | 1.30899 rad | 1.30923 | 0.00896 |
| θ | 0.54409 rad | 0.55009 | |

As shown in the above table, the averages of the reconstructed values correspond very well to the actual values for thickness and orientation. This result is attributable to the fact that accurate measurements of thickness and orientation can be made with velocity errors up to 1%, according to exemplary embodiments of the invention. In addition, the standard deviations for the reconstructed values are exceptionally low, which illustrates the effectiveness of the above method. The method is also relatively insensitive to the initial estimates of the thickness and orientation angles, which can be as large as±40% of the actual values.

Figure 13:
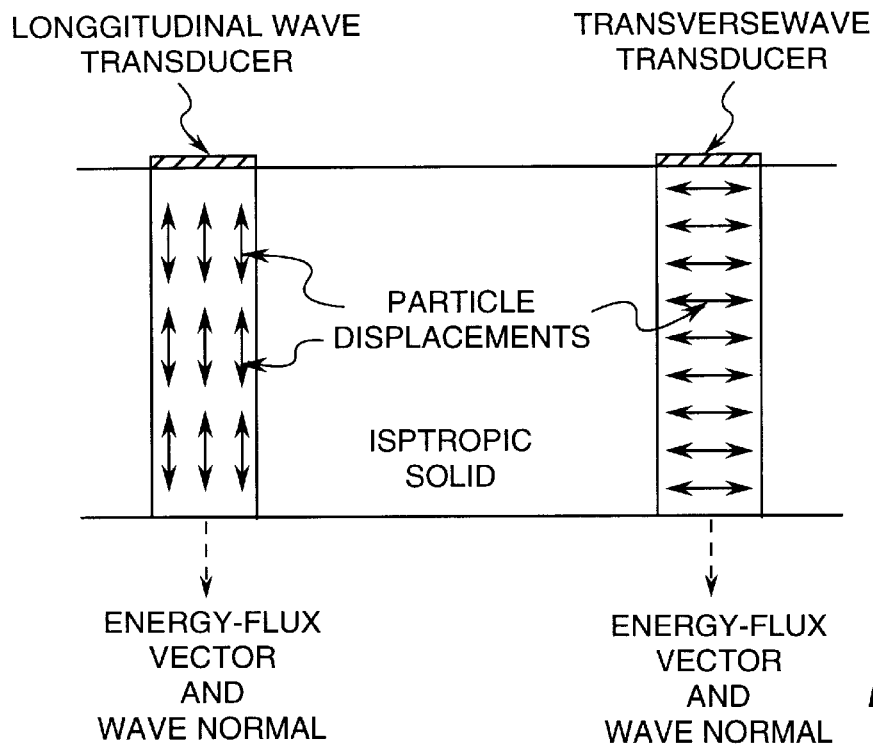
FIG. 13 illustrates the relationship between the energy flux vector and the wave normal in an isotropic solid.
Figure 14:
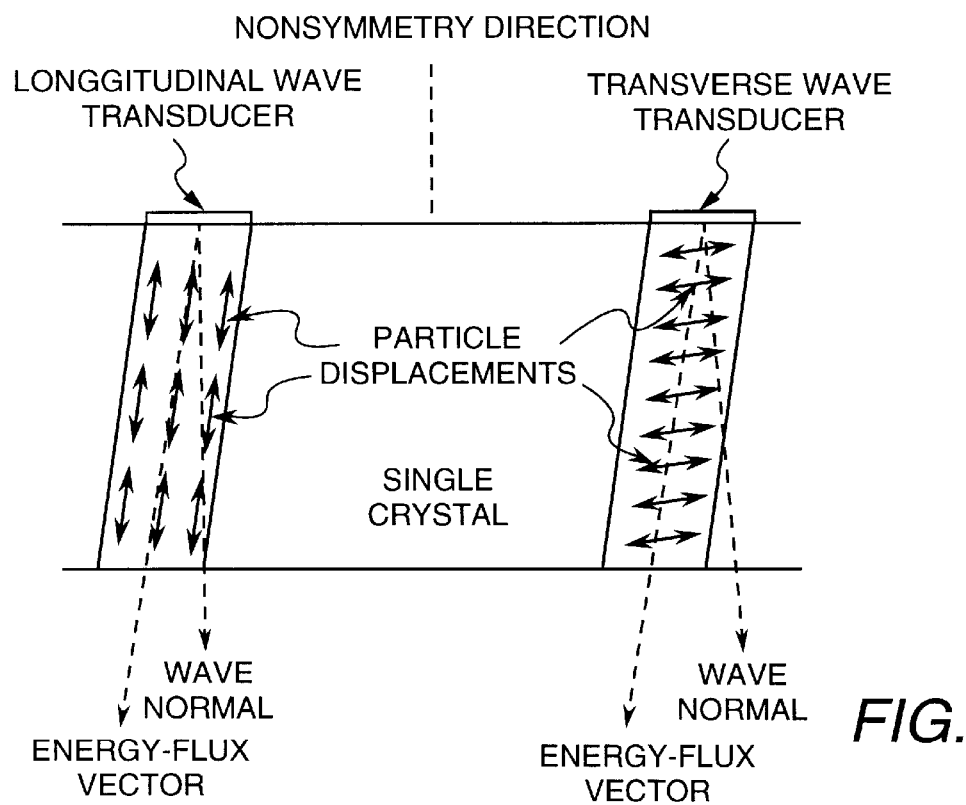
FIG. 14 illustrates the relationship between the energy flux vector and the wave normal in an anisotropic solid.

Thickness measurement in anisotropic media is further complicated by the phenomenon of "beam skew". Beam skew is the well known observation that, unlike in an isotropic medium, the direction of energy propagation in an anisotropic medium will not necessarily correspond to the wave normal unless the wave normal corresponds with a symmetry direction of the medium. This phenomenon is illustrated in FIG. 13, which shows propagation through an isotropic medium, and FIG. 14, which shows propagation through an anisotropic medium. Considerable care is required in making accurate velocity measurements in anisotropic media because of the presence of beam skew.

Figure 15:
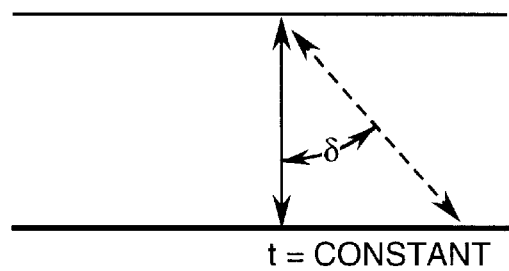
FIGS. 15–16 illustrate the effects of beam skew on the measurement of thickness.

As long as the test medium is a flat plate with parallel reflecting surfaces, beam skew effects can be neglected. This is because energy propagates with the group velocity $V_g$, rather than the phase (wave) velocity $V_p$. The phase and group velocities are related by the following equation:

$$V_p = V_g \cos\delta \quad (13)$$

where $\delta$=beam skew angle. In addition, as shown in FIG. 15, the acoustic transit time for the acoustic wave in the presence of beam skew is given by:

$$\Delta T = \frac{2t}{V_g \cos\delta} \quad (14)$$

where $\Delta T$=transit time and t=thickness. Thus, substituting equation (13) into equation (14) yields $$\Delta T = \frac{2t}{v_p} \quad (15)$$

which is the same equation as for an isotropic material.

Figure 16:
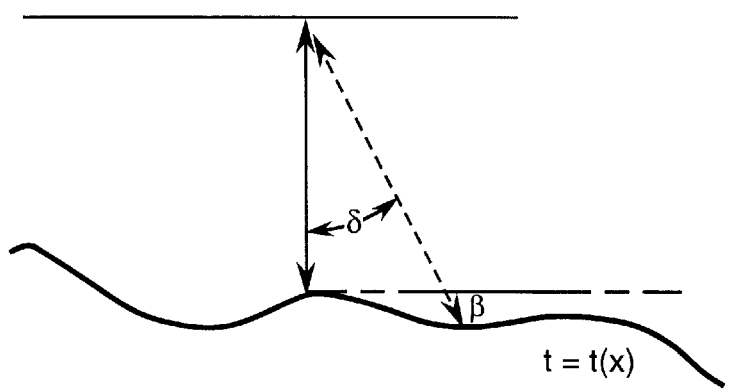

When the part surfaces are not flat and parallel, however, there is an additional component $\beta$ in the ray path, as shown in FIG. 16, which is not accounted for in the above analysis. This discrepancy is a potentially large source of error in measuring thickness in curved anisotropic parts.

The phenomenon of beam skew may be accounted for by modeling the changes in the direction and speed of energy propagation introduced by material anisotropy. The effects of beam skew on the predicted transit times may then be accounted for by modeling the shape of the back surface of the test medium being measured. For example, the additional component $\beta$ can be factored into the equation used to predict wave transit time when the effects of beam skew are taken into account.

The equation for energy propagation in an anisotropic medium is as follows:

$$S_j = \frac{C_{ijkl} l_l \alpha_i \alpha_k}{\rho v} \quad (16)$$

where $S_j$=components of the energy flex vector, $C_{ijkl}$ is the stiffness matrix, $\alpha$ is the polarization vector, 1 is the wave normal, $\beta$ is the density, and v is the phase velocity. In equation (16), $|S|=v_g$=group velocity, $S/|S|$=direction of energy propagation, and $S \cdot l = v_p$=phase velocity. From this equation it is possible to determine the path and velocity of acoustic wave propagation in an anisotropic medium.

In order to align the coordinate axes of the stiffness matrix with the geometry of the test medium to be measured, it is useful to transform the stiffness matrix components Cijkl. The stiffness matrix may be rotated such that the new Z axis is aligned normal to the surface of the test medium, and the X and Y axes are tangent to the surface of the test medium, for example. The original stiffness tensor matrix can be transformed with the following equation:

$$C^1_{ijkl} = a_{i\alpha} a_{j\beta} a_{k\gamma} a_{i\delta} C_{\alpha\beta\gamma\delta} \quad (17)$$

where the rotation matrix is given by:

$$a_{ij} = \begin{bmatrix} \sin\theta\cos\varphi & \sin\varphi & \cos\theta\cos\varphi \\ \sin\theta\sin\varphi & -\cos\varphi & \cos\theta\sin\varphi \\ \cos\theta & 0 & -\sin\varphi \end{bmatrix} \quad (18)$$

Once the wave normal is specified for the wave under consideration, the velocity and direction of energy propagation can be calculated with equation (16).

Figure 17:
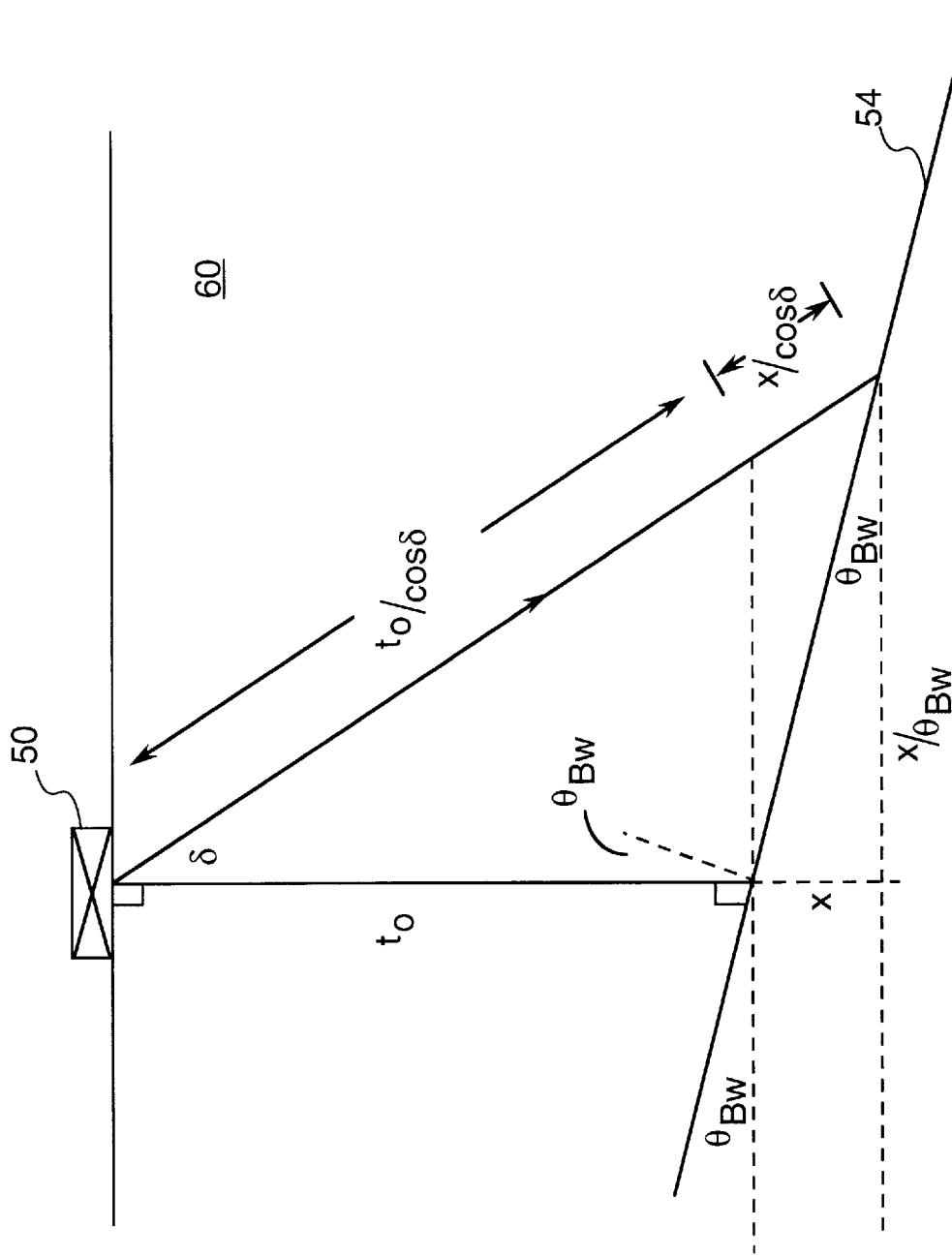
FIGS. 17–18 illustrate a method of compensating for beam skew in a test medium having flat, nonparallel surfaces.
Figure 18:
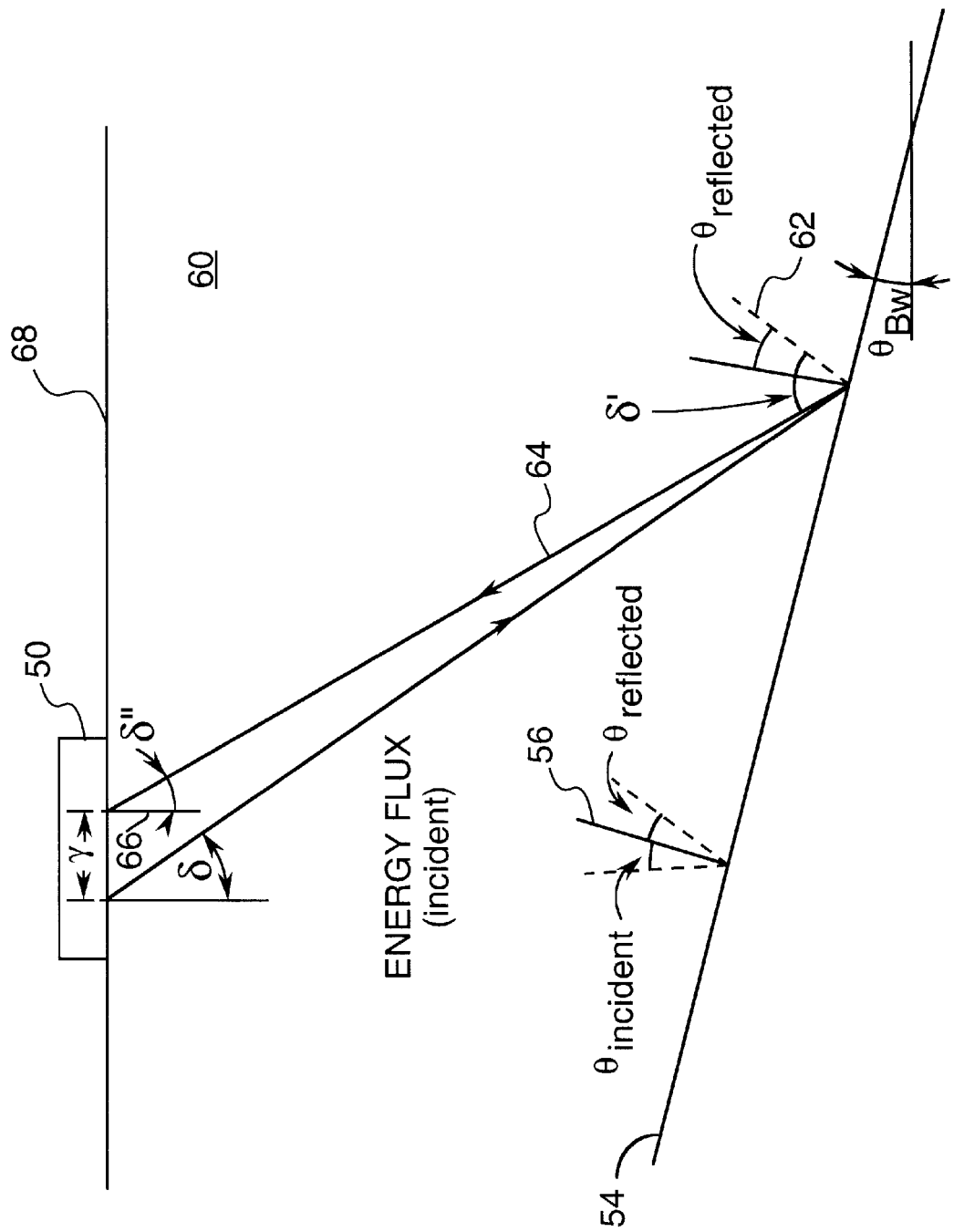

The effects of beam skew on the transit time predictions may be taken into account by modeling the shape of the part being measured. Various geometric models of differing complexity may be used. According to one embodiment, the front and back surfaces of the test medium are modeled as locally flat, in a piece-wise fashion, but not parallel to one another ("the piecewise-flat model"). The geometry for the piece-wise flat model is shown in FIG. 17 for the outbound wave transmitted by the transducer 50 which is incident on the back surface 54 of the test medium 60. The geometry for the inbound ray returning to the transducer 50 after being reflected off the back surface 54 of the test medium 60 is shown in FIG. 18. The rays are shown separately for clarity and to delineate how the back surface reflection is treated when anisotropy is present. If the back wall angle $\theta_{BW}$ is known from the geometry of the test medium 60, the thickness and two orientation angles can be determined.

For the outgoing ray from the transducer 50, the transit time to the back surface 54 is calculated using $\theta_{BW}$ as well as the group velocity vg and beam skew angle $\delta$ for the crystal orientation and mode of propagation under consideration. For this case, as shown in FIG. 17, the travel time $\Delta T$ to the back surface is:

$$\Delta T_{incident} = \frac{(t_o + x)/\cos\delta}{Vg_{incident}} \quad (19)$$

where $t_o$=thickness and x is determined from the following relationship for similar triangles:

$$\frac{t_0 + x}{t_0} = \frac{x\tan\theta_{BW}}{t_0 \tan\delta} \quad (20)$$

The group velocity $V_g$ and beam skew angle $\delta$ are calculated using equation (16).

To determine the velocity of the inbound ray reflected off the back surface 54 of the test medium 60, the wave normal 56 of the inbound ray may be determined using Snell's law:

$$\frac{\sin\theta_{incident}}{V_{\rho\, incident}} = \frac{\sin\theta_{reflected}}{V_{\rho\, reflected}} \quad (21)$$

The application of Snell's law in an anisotropic medium is more complicated than for the corresponding case in an isotropic medium, since the velocity is directionally dependent. Snell's law is thus solved in conjunction with the Christoffel equation as described, for example, in Ronald A. Kline, *Nondestructive Characterization of Composite Media*, Technomic Publishing Co. (1992).

Once the reflected wave normal is determined, the new beam skew angle δ' can be calculated with equation (16) for the reflected wave. The new beam skew angle δ' is the angle between the reflected wave normal 62 and the direction of energy propagation of the reflected wave 64. The new beam skew angle δ' can then be used to calculate δ", the angle between the direction of energy propagation of the reflected wave 64 and the normal 66 to the front surface 68 of the test medium 60. The return transit time is given by:

$$\Delta T_{reflected} = \frac{(t_0 + x)/\cos\delta'}{V_{g\, reflected}} \quad (22)$$

Equations (19) and (22) can thus be used in calculating the predicted transit time of a particular wave propagating through an anisotropic test medium where the front and back surfaces 68 and 54 are flat but not parallel to each other. In the case of a test medium 60 which is piecewise flat, equations (19) and (22) may be incorporated into the method illustrated in FIG. 11 in step 502. Step 506 may be modified to include equations (19) and (22) in calculating the predicted transit times.

In general, the reflected wave will not return to the same point from which it was originally transmitted into the test medium 60 but instead will be displaced by a distance γ as shown in FIG. 18. Therefore, the radius of the transducer 50 is preferably at least equal to γ to sense the returned echo.

The parameter or parameters which characterize the back surface of the test medium, e.g. $\theta_{BW}$, can be obtained from additional ultrasonic measurements. The desired number of measurements depends on the shape of the back surface and the degree to which the thickness changes in the vicinity of the inspection site. For example, if the back surface is flat, one additional measurement can be made to determine $\theta_{BW}$, the angle between the front and back surfaces 68 and 54 of the test medium.

For additional accuracy, a polynomial model can be used to represent the back surface contour:

$$t(x) = t_0 + t_1 x + t_2 x^2 + t_3 x^3 \quad (23)$$

In the above equation, $t_0$ represents the thickness of the test medium at the measurement site, and the remaining parameters $t_i$ establish the back surface shape. Higher order polynomials result in higher accuracy in the representation of the back surface. The higher order polynomials representing the back surface contour may be obtained by taking additional measurements for the additional parameters to be reconstructed, e.g. one for each of the additional polynomial surface representation parameters $t_i$.

According to one example, the front and back surfaces of the test medium to be measured are modeled as concentric cylinders. This model may be useful in certain applications in which the articles being measured are generally cylindrical in shape.

Figure 19:
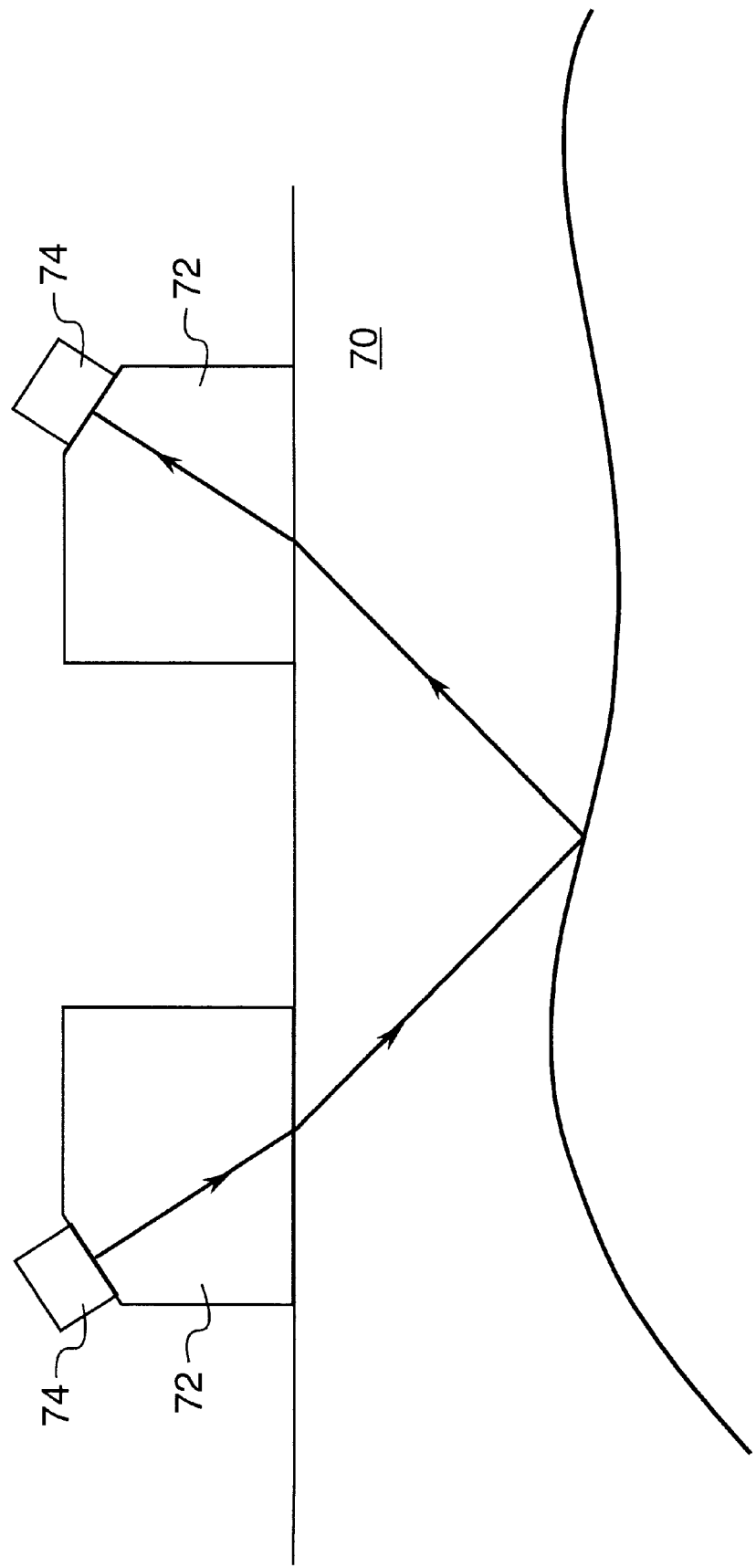
FIG. 19 illustrates a method and apparatus for reconstructing a contour of a back surface of the test medium.

According to a preferred embodiment, the measurements used to construct a model for the contour of the back surface may be obtained with the exemplary apparatus shown in FIG. 19, which includes two wedges 72 instrumented with piezoelectric transducers 74. Either longitudinal or shear transducers can be used. Each different wedge angle results in a unique ray path. With a sufficiently large number of wedges of different wedge angle, a sufficient number of independent rays are introduced into the test medium 70 to reconstruct any back surface shape. The same result can be accomplished in immersion by rotating the generating and receiving transducers in tandem to different incident angles to produce multiple independent waves. In addition, the polarization of the shear waves having the same incident angle may be changed to obtain additional measurement data. Additional measurements can be utilized to oversample and reduce the effects of measurement error on the thickness reconstructions.

The wave transit time measurements and the wedge angles are used in conjunction with Snell's law and the Christoffel equation to construct a model of the back surface of the test medium. The model which describes the contour of the back surface of the test medium may be incorporated into the exemplary methods described above for determining thickness and orientation, by adjusting the predicted wave transit times to account for beam skew and the geometry of the test medium.

According to another embodiment of the invention, the anisotropic (e.g., crystal) orientation and thickness may be directly measured in a test medium having non-parallel front and back surfaces without compensating for the effects of beam skew. The invention according to this embodiment includes a spherical transducer which focuses an incident longitudinal wave at the front surface of the test medium.

Figure 20:
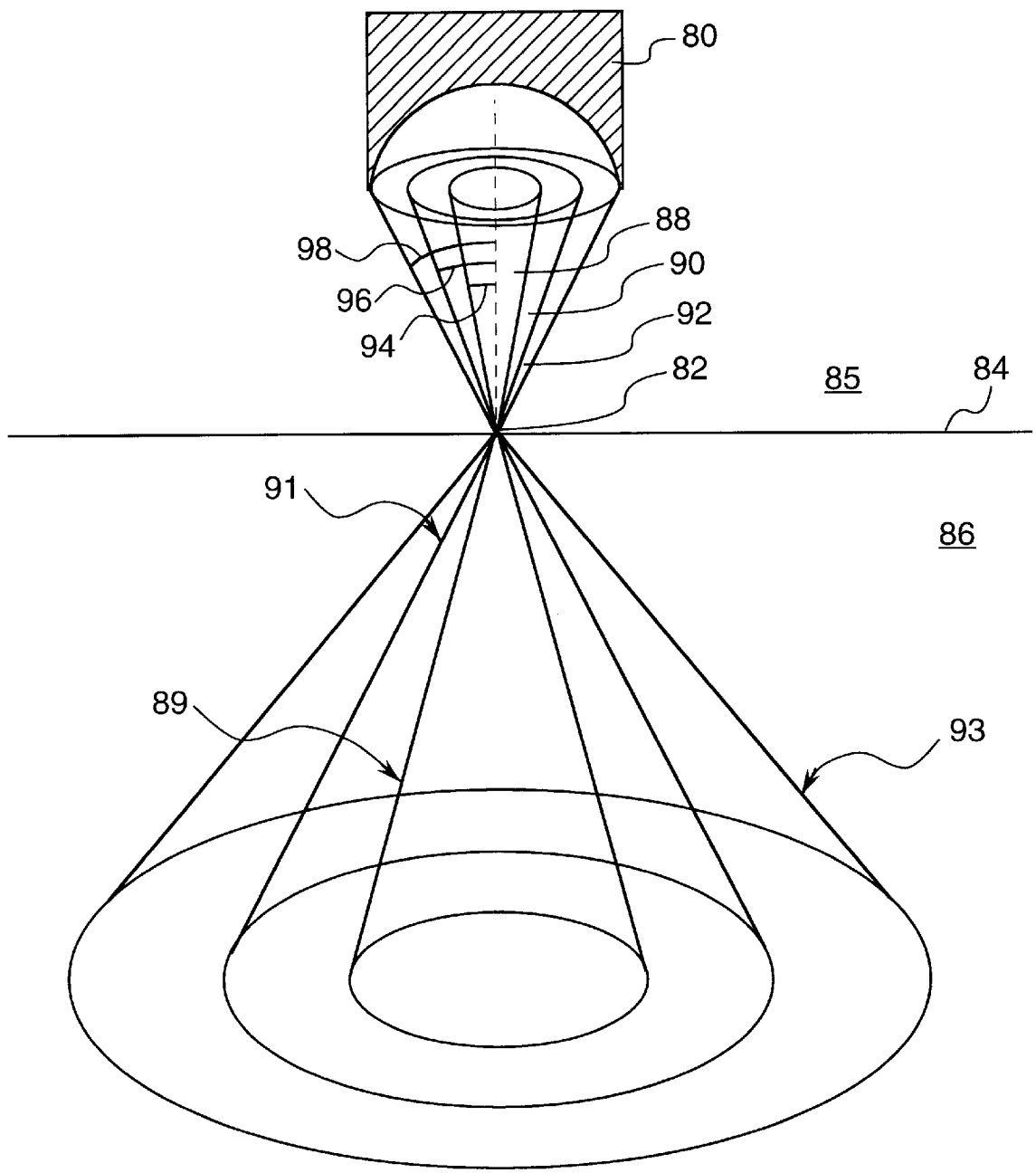
FIG. 20 illustrates wave propagation from a spherical transducer.

As shown in FIG. 20, the spherical transducer 80 generates an incident waveform which includes components over a range of incident angles focused at a point 82 on the front surface 84 of the test medium 86. The incident wave, which may be a longitudinal wave, generates both longitudinal and shear waves in the test medium 86 through mode conversion. The spherical transducer 80 and the test medium 86 may be immersed in a fluid 85 such as water to acoustically couple the transducer 80 to the test medium 86.

The angle of incidence (measured from the surface normal) of the incident wave component determines the characteristics of the waves which are transmitted through the test medium 86. For the rays in the converging beam that are at a nonzero angle of incidence, an incident longitudinal wave generates a transmitted longitudinal wave and orthogonal fast and slow shear waves. As the angle of incidence of the incident longitudinal wave increases, the transmitted waves reach a first critical angle 94 beyond which only the fast and slow shear waves are generated in the test medium. As the angle of incidence increases further, a second critical angle 96 is reached, beyond which only the slow shear wave is generated in the test medium. As the angle of incidence increases still further, a third critical angle 98 is reached, beyond which no acoustic waves penetrate the test medium, i.e, total reflection occurs. By way of example, for a nickel based superalloy in water, the spherical transducer is configured to generate an incident, focused wave over a range of about 43 degrees from the surface normal to produce the desired longitudinal and shear waves in the test medium.

As shown in FIG. 20, the range of incident angles produced by the transducer 80 can be divided into three portions, represented by concentric cones. A first portion 88 is incident on the test medium 86 over a range of angles less than the first critical angle 94 so that a refracted wave cone 89 is generated in the test medium 86 which includes longitudinal, fast shear, and slow shear waves. A second portion 90 is incident on the test medium 86 over a range of angles between the first and second critical angles 94 and 96 so that a refracted wave cone 91 is generated in the test medium 86 which includes fast and slow shear waves. A third portion 92 is incident on the test medium 86 over a range of angles greater than the second critical angle 96 so that a refracted wave cone 93 is generated in the test medium 86 which includes a slow shear wave.

Because the transducer 80 is spherical, these components can be generated simultaneously with a single pulse, rather than sequentially as with a flat transducer. The transducer 80 thus preferably generates wave components over a range of incident angles which is great enough to generate the three wave modes in the particular medium being tested. The transducer 80 generates three refracted ray cones 89, 91, 93 in the anisotropic sample 86 corresponding to the three modes of propagation which have three wave speeds.

Figure 21:
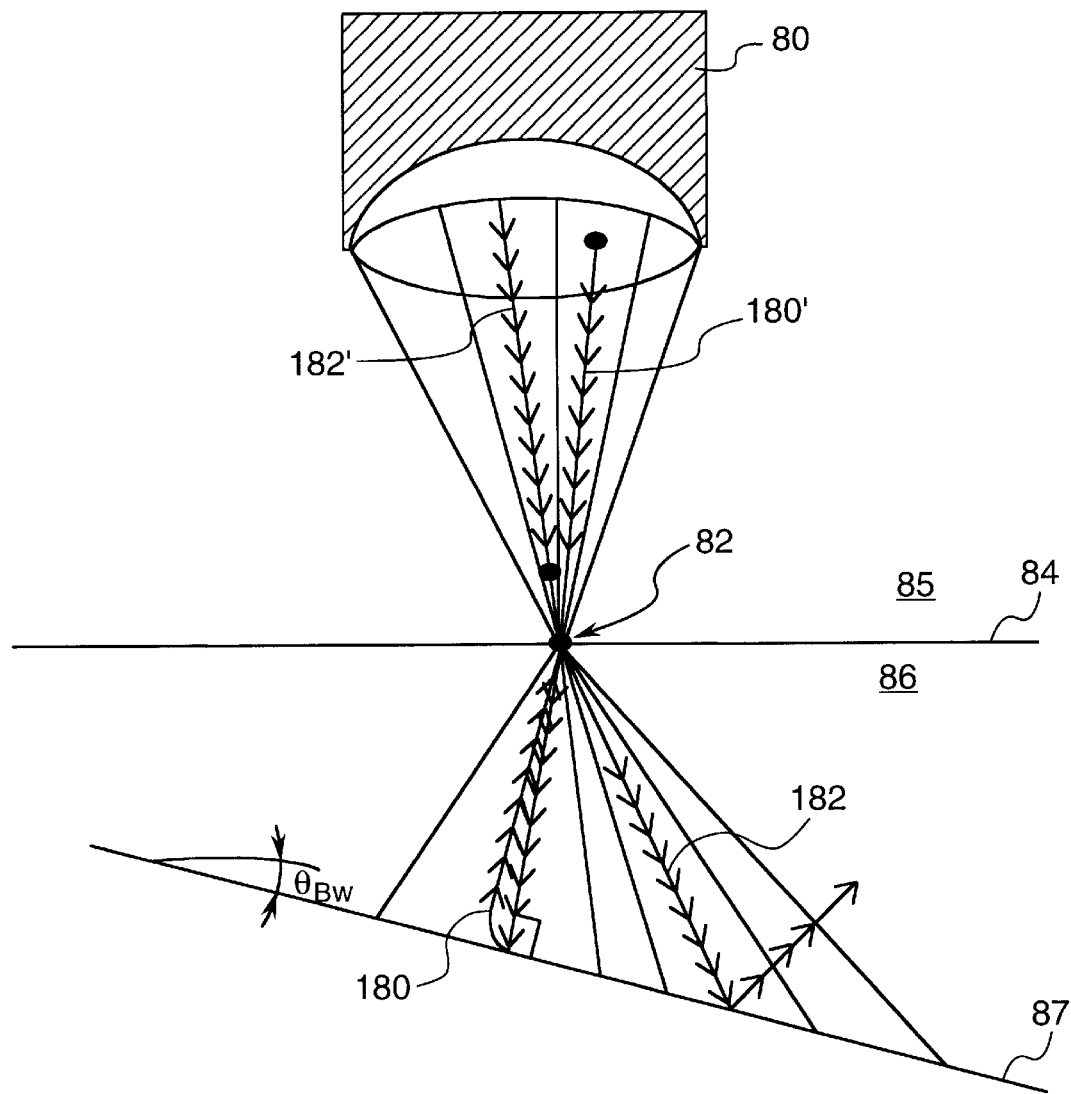
FIGS. 21–22 illustrate the reflection of longitudinal and shear waves perpendicular to the back surface of the test medium.

From the cone of refracted rays, the strongest signal reflected back to the transducer 80 will be from the ray having a wave normal perpendicular to the back surface of the test medium. This reflected signal is shown in FIG. 21 where rays 180 normal to the back surface 87 are reflected directly back to the transducer 80 while rays 182 which are oblique to the back surface diverge. From each refracted cone, there is one and only one angle which satisfies both Snell's law and is perpendicular to the back surface, i.e., $$\sin\theta_L = \frac{v_W}{v_L}\sin\theta_{BW}, \quad (24a)$$

$$\sin\theta_{FS} = \frac{V_W}{V_{FS}}\sin\theta_{BW} \quad (24b)$$

$$\sin\theta_{SS} = \frac{V_W}{V_{SS}}\sin\theta_{BW} \quad (24c)$$

where v indicates phase velocity, $\theta_{BW}$ is the common refracted angle for all three modes, and the remaining angles $\theta$ are the angles of incidence with the subscripts L, FS, SS, and W corresponding to the longitudinal, fast shear, slow shear, and water, respectively.

Figure 22:
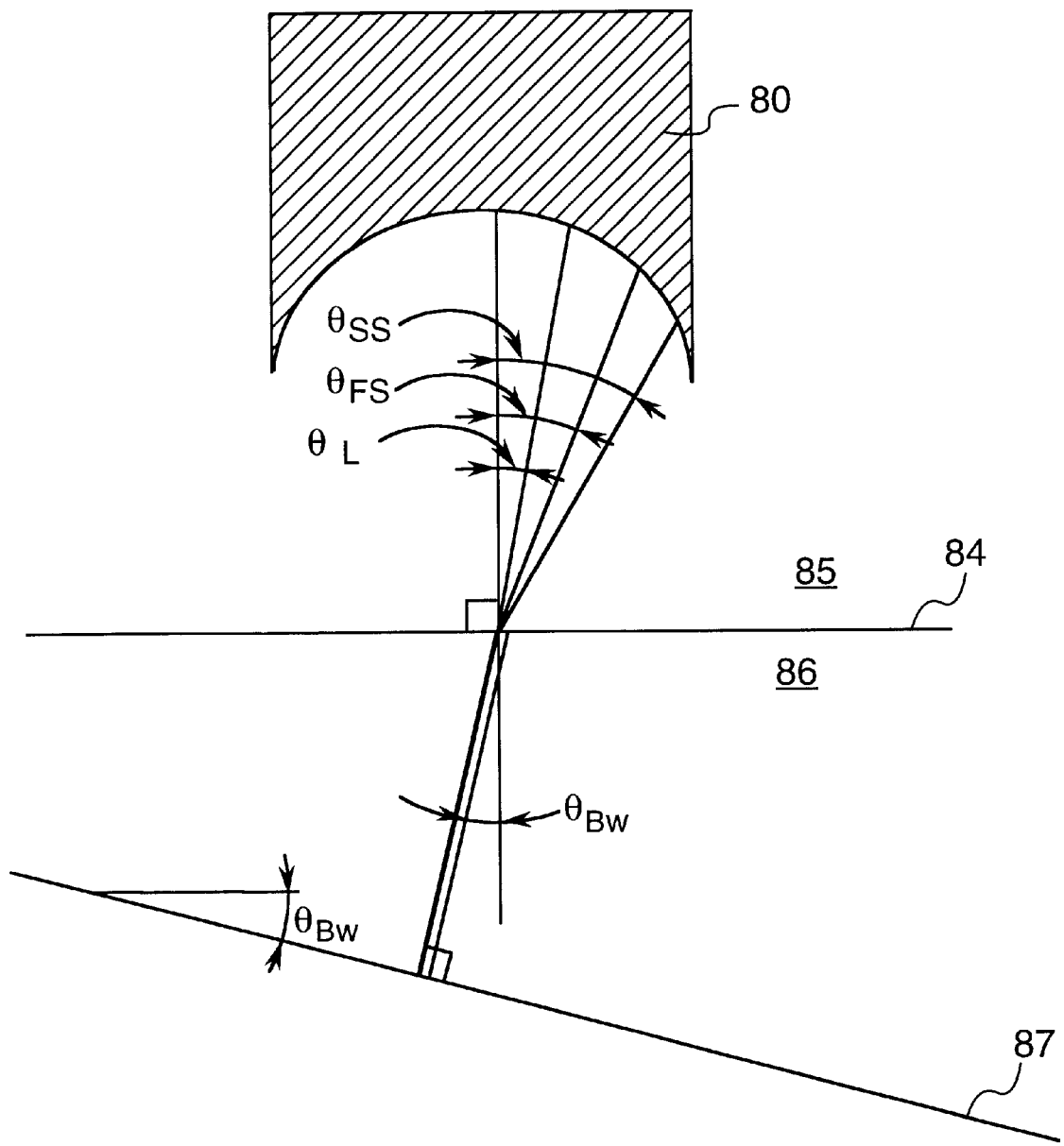

These three rays all return to the transducer along their original paths, as shown in FIG. 22. As they all have different velocities of propagation (unless the back wall normal is a symmetry direction) there will be three distinct signals in the sensed waveform. The thickness of the test medium 86, measured along the perpendicular to the front surface 84, can be derived from $\theta_{BW}$ and the distance from the back surface 87 to the front surface 84, measured along the perpendicular to the back surface 84.

A significant advantage of this exemplary method is that beam skew effects are automatically taken into account. Just as in the case of a test medium with flat, parallel front and back surfaces (e.g. FIG. 15), the phase velocity transit time in the direction of the surface normal is measured directly so that no beam skew compensation is necessary. The measurements of the transit times for the refracted waves are used as input to the methods discussed above and illustrated, for example, in FIGS. 6 and 11.

While the invention has been described with reference to preferred embodiments, those skilled in the art will understand that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiments disclosed as the best mode contemplated for carrying out this invention, but that the invention will include all embodiments falling within the scope of the appended claims.

What is claimed is:

1. An apparatus for determining an anisotropic orientation of an article, the apparatus comprising:

means for propagating a first wave and a second wave through the article;

means for measuring a respective transit time of the first wave and the second wave propagating through the article;

means for calculating a respective predicted transit time of the first wave and the second wave based on an estimated anisotropic orientation and an elasticity of the article; and means for adjusting the estimated anisotropic orientation to reduce a difference between the respective measured transit time and the respective predicted transit time of the first and second waves.

2. The apparatus of claim 1, wherein the means for propagating is adapted to propagate two of the following three waves: a longitudinal wave, a first transverse wave having a first polarization, and a second transverse wave having a second polarization.

3. The apparatus of claim 1, wherein the means for propagating comprises at least one ultrasonic transducer.

4. The apparatus of claim 1, further comprising an immersion tank for immersing the article and the means for propagating in a fluid.

5. The apparatus of claim 1, wherein the means for adjusting the estimated anisotropic orientation is adapted to subtract a square of the respective measured transit time from a square of the respective predicted transit time for each of the first and second waves to reduce the difference between the respective measured transit time and the respective predicted transit time of the first and second waves.

6. The apparatus of claim 1, wherein the means for adjusting utilizes a Levenberg-Marquardt iteration.

7. A method of determining a thickness and an anisotropic orientation of an anisotropic article comprising the steps of:

propagating first, second, and third waves through the article;

measuring a respective transit time of each of the first, second, and third waves propagated through the article;

estimating respective values for the thickness of the article and the anisotropic orientation of the article;

calculating a respective predicted transit time of the first, second, and third waves based on the estimated values for the thickness and the anisotropic orientation, and based on an elasticity of the article; and adjusting the estimated values for the thickness and the anisotropic orientation to reduce a difference between the measured transit time and the predicted transit time of the first, second, and third waves.

8. The method of claim 7, wherein the first wave comprises a longitudinal wave, the second wave comprises a transverse wave having a first polarization, and the third wave comprises a transverse wave having a second polarization.

9. The method of claim 7, further comprising the steps of:

propagating a fourth wave through the article;

measuring a transit time of the fourth wave propagated through the article; and adjusting the estimated values for the thickness and the anisotropic orientation based on the measured transit time of the fourth wave.

10. The method of claim 7, wherein the step of propagating the first, second, and third waves is carried out with at least one piezoelectric transducer.

11. The method of claim 7, wherein the step of propagating the first, second, and third waves comprises the steps of:

propagating a longitudinal wave through a fluid which surrounds the article; and mode converting the longitudinal wave into the first, second, and third waves.

12. The method of claim 11, wherein the step of propagating the longitudinal wave comprises activating a spherical transducer which focuses the longitudinal wave at a point on a surface of the article.

13. The method of claim 7, wherein the difference between the measured transit time of the first, second, and third waves and the respective predicted transit time of the first, second, and third waves is measured by subtracting a square of the respective measured transit time from a square of the respective predicted transit time for each of the first, second, and third waves.

14. The method of claim 7, further comprising the step of measuring a relative transit time of the first, second, and third waves at a different location on the article with a phase locked loop.

15. An apparatus for determining a thickness and an anisotropic orientation of an article comprising:

means for measuring a respective transit time of a first, second and third wave propagating through the article;

means for calculating a respective predicted transit time of the first, second, and third waves based on estimated values of the thickness and the anisotropic orientation, and based on an elasticity of the article; and means for adjusting the estimated values for the thickness and the anisotropic orientation to reduce a difference between the respective measured transit time of the first, second, and third waves and the respective predicted transit time of the first, second, and third waves.

16. The apparatus of claim 15, wherein the means for measuring a transit time comprises at least one piezoelectric transducer.

17. The apparatus of claim 15, wherein the means for measuring a transit time comprises an electromagnetic acoustic transducer.

18. The apparatus of claim 15, wherein the means for measuring a transit time comprises a spherical transducer.

19. The apparatus of claim 18, wherein the spherical transducer comprises a spherically curved element.

20. The apparatus of claim 18, wherein the spherical transducer comprises a lens.

21. The apparatus of claim 15, further comprising a positioning member which movably positions the means for measuring a transit time at different locations with respect to the article.

22. The apparatus of claim 15, further comprising a tank, wherein the article and the means for measuring a transit time are disposed within the tank.

23. An apparatus for determining a thickness and an anisotropic orientation of an article, the apparatus comprising:

a transducer assembly which generates first, second, and third waves in the article, and which receives reflections of the first, second and third waves;

a transceiver, connected to the transducer, which generates a signal to activate the transducer assembly and which receives a signal representative of the reflections of the first, second, and third waves from the transducer assembly; and a computer, connected to the transceiver, which commands the transceiver to generate the signal to activate the transducer and which receives from the transceiver a signal representative of the reflections of the first, second, and third waves, the computer being adapted to determine respective transit times for the first, second and third waves; receive estimated values for the thickness and the anisotropic orientation of the article; receive elastic properties of the article; calculate respective predicted transit times of the first, second, and third waves based on the estimated values for the thickness and the anisotropic orientation and based on the elastic properties; and adjust the estimated values for the thickness and the anisotropic orientation to reduce a difference between the respective measured transit time and the respective predicted transit time of the first, second and third waves.

24. The apparatus of claim 23, wherein the transducer assembly comprises:

a longitudinal transducer which generates a longitudinal wave; and a shear transducer which generates a transverse wave.

25. The apparatus of claim 23, wherein the transducer assembly comprises a spherical transducer.

26. The apparatus of claim 25, wherein the spherical transducer comprises a spherically curved element.

27. The apparatus of claim 25, wherein the spherical transducer comprises a lens.

28. The apparatus of claim 25, wherein the spherical transducer is adapted to generate a conical longitudinal wave which is focused at a point on a surface of the article to generate a refracted longitudinal wave and a refracted transverse wave in the article.

29. The apparatus of claim 28, further comprising:

an immersion tank for immersing the article; and a positioning mechanism which movably positions the transducer assembly with respect to the article.

30. The apparatus of claim 23, further comprising a signal digitizer which digitizes the signal representative of the reflections of the first, second, and third waves prior to sending the signal to the computer.

31. A method for determining an anisotropic orientation of an article comprising the steps of:

measuring a respective velocity of a first wave and a second wave propagating through the article;

estimating the anisotropic orientation of the article;

calculating a respective predicted velocity of the first wave and the second wave based on the estimated anisotropic orientation and an elasticity of the article; and adjusting the estimated anisotropic orientation to reduce to below a predetermined value a difference between the respective measured velocity of the first and second waves and the respective predicted velocity of the first and second waves.

32. The method of claim 31, wherein the first and second waves comprise two of the following three waves: a longitudinal wave, a first transverse wave having a first polarization, and a second transverse wave having a second polarization.

33. The method of claim 31, wherein the step of measuring a velocity comprises the steps of:

propagating the first wave and the second wave through the article; and measuring a respective transit time of the first wave and of the second wave.

34. The method of claim 31, wherein the step of measuring the velocity comprises the steps of:

contacting the article with a material of known acoustic impedance;

propagating an incident wave through the material to the article;

measuring an amplitude of a reflected wave reflected from an interface between the article and the material;

measuring an amplitude of a transmitted wave transmitted through the interface;

calculating the velocity of the transmitted wave based on the acoustic impedance of the material and the amplitudes of the reflected and transmitted waves.

35. The method of claim 31, wherein the step of measuring the velocity of the first wave comprises the steps of:

contacting the article with a material;

propagating an incident wave in the material to the article;

determining a critical angle at which the incident wave is completely reflected at an interface between the material and the article;

calculating the velocity of the first wave based on the critical angle.

36. The method of claim 31, wherein the step of measuring the velocity of the first wave comprises the steps of:

propagating the first wave across a surface of the article;

measuring a travel time of the first wave over a predetermined distance; and calculating the velocity of the first wave based on the travel time and the predetermined distance.

37. An apparatus for determining an anisotropic orientation of an article, the apparatus comprising:

a transducer assembly for propagating a first wave and a second wave through the article in a direction defined by a wave normal; and a processor, connected to the transducer, which measures a respective transit time for the first and second waves; calculates a respective direction of energy propagation for the first and second waves relative to the wave normal; and calculates the anisotropic orientation of the article based on the respective measured transit time and the respective direction of energy propagation of the first and second waves.

38. The apparatus of claim 37, wherein the transducer assembly is adapted to propagate a third wave through the article, and the processor is adapted to measure a transit time of the third wave, calculate a direction of energy propagation for the third wave relative to the wave normal, and calculate a thickness of the article based on the respective measured transit time and the respective direction of energy propagation of the first, second, and third waves.

39. The apparatus of claim 37, wherein the processor is adapted to calculate the anisotropic orientation of the article based on a model of the shape of the article.

40. The apparatus of claim 39, wherein the shape of the article is modeled as having planar front and back surfaces, which surfaces are not parallel to each other.

41. The apparatus of claim 39, wherein the shape of the article is modeled as having concentric cylindrical surfaces.

42. The apparatus of claim 39, wherein the shape of the article is modeled as having a back surface defined by a polynomial.

* * * * *